(12) United States Patent  
Park et al.

(10) Patent No.: US 12,352,073 B2
(45) Date of Patent: Jul. 8, 2025

(54) DOOR HANDLE

(71) Applicant: LG ELECTRONICS INC., Seoul (KR)

(72) Inventors: Jaeyong Park, Seoul (KR); Junghan Ryu, Seoul (KR); Kyu-Suh Park, Seoul (KR); Hwa Suk Shim, Seoul (KR); Hyun Chul Kim, Seoul (KR); Jung Hoon Lee, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 169 days.

(21) Appl. No.: 18/020,357

(22) PCT Filed: Feb. 2, 2021

(86) PCT No.: PCT/KR2021/001380
§ 371 (c)(1),
(2) Date: Feb. 8, 2023

(87) PCT Pub. No.: WO2022/045496
PCT Pub. Date: Mar. 3, 2022

(65) Prior Publication Data
US 2023/0304318 A1 Sep. 28, 2023

(30) Foreign Application Priority Data

Aug. 26, 2020 (KR) .................. 10-2020-0108173

(51) Int. Cl.
*E05B 85/10* (2014.01)
*A61L 2/10* (2006.01)
(Continued)

(52) U.S. Cl.
CPC .............. *E05B 1/0069* (2013.01); *A61L 2/10* (2013.01); *A61L 2/24* (2013.01); *E05B 5/003* (2013.01)

(58) Field of Classification Search
CPC .... Y10T 292/57; Y10T 292/82; Y10S 292/31; E05B 1/00; E05B 1/0007; E05B 1/0038;
(Continued)

(56) References Cited

U.S. PATENT DOCUMENTS 5,029,916 A * 7/1991 Chiu ..................... E05B 1/0038
292/336.3
7,989,779 B1 * 8/2011 Ray ........................... A61L 2/10
250/493.1
(Continued)

FOREIGN PATENT DOCUMENTS

DE 3427178 A1 * 2/1986
DE 102009050080 A1 * 4/2011 ............... A61L 2/10
(Continued)

*Primary Examiner* — Carlos Lugo
(74) *Attorney, Agent, or Firm* — Birch, Stewart, Kolasch & Birch, LLP

(57) ABSTRACT

The present invention relates to a door handle and, more specifically, to a door handle which may comprise: a housing which is fixed to a door and has an inner space; a drive part which supplies rotational power; a rotating guide which is connected to the drive part to receive rotational power therefrom and rotate within the housing; and a handle part which is disposed within the rotating guide, and protrudes out of the housing by forward rotation of the rotating guide and is retracted into the housing by reverse rotation of the rotating guide.

21 Claims, 19 Drawing Sheets

(51) Int. Cl.
*A61L 2/24* (2006.01)
*E05B 1/00* (2006.01)
*E05B 5/02* (2006.01)

(58) Field of Classification Search
CPC ........ E05B 1/0069; E05B 1/0092; E05B 5/00; E05B 5/003; E05B 85/103; E05B 65/0014; E05C 1/14
See application file for complete search history.

(56) References Cited

U.S. PATENT DOCUMENTS

| | | | | |
|---|---|---|---|---|
| 8,701,353 | B2 * | 4/2014 | Patel | E05B 85/103 |
| | | | | 292/201 |
| 8,733,815 | B2 | 5/2014 | Kwon | |
| 8,919,047 | B2 * | 12/2014 | Johnsrud | E05B 85/103 |
| | | | | 292/336.3 |
| 8,978,428 | B2 * | 3/2015 | Trent | E05B 47/0012 |
| | | | | 70/279.1 |
| 10,619,378 | B2 | 4/2020 | Wind et al. | |
| 2012/0128344 | A1 | 5/2012 | Kwon | |
| 2015/0059424 | A1 | 3/2015 | Hunt | |
| 2018/0216364 | A1 | 8/2018 | Wind et al. | |
| 2020/0240172 | A1 | 7/2020 | Wind et al. | |

FOREIGN PATENT DOCUMENTS

| | | | | |
|---|---|---|---|---|
| DE | 102009050081 A1 * | 4/2011 | | A61L 2/10 |
| DE | 102017006838 A1 * | 1/2019 | | |
| EP | 3290623 A1 * | 3/2018 | | E05B 13/10 |
| GB | 2275496 A * | 8/1994 | | E05B 13/005 |
| JP | 2016-93470 A | 5/2016 | | |
| KR | 10-2009-0090025 A | 8/2009 | | |
| KR | 10-1219398 B1 | 1/2013 | | |
| KR | 10-1740189 B1 | 5/2017 | | |
| KR | 102122711 B1 * | 6/2020 | | |

* cited by examiner

DOOR HANDLE

This application is the National Phase of PCT International Application No. PCT/KR2021/001380 filed on Feb. 2, 2021, which claims priority to and the benefit of Korean Patent Application No. 10-2020-0108173 filed on Aug. 26, 2020, the disclosures of which are incorporated herein by reference in their entirety.

TECHNICAL FIELD

The present invention relates to a door handle capable of blocking transmission of pathogens by automatically sterilizing a handle part.

BACKGROUND ART

In general, a door handle is a handle installed on a door, and the door is opened or closed by a user pulling or pushing the door handle. The door is installed in an entrance of a building, and the door handle may be installed on both outer and inner sides of the door.

The door handle is installed on the outer side of the door in a protruding state, and the user grasps the door handle and moves the door.

Conventionally, since many unspecified people grasp the door handle and move the door, there is a problem that the door handle is contaminated with pathogens including viruses. In addition, when disinfection light is emitted to disinfect the door handle, there is a problem that the disinfection light may be emitted to the user, which causes injury to the user. Accordingly, this problem needs to be addressed.

The related art of the present invention is disclosed in Korean Patent Publication No. 10-2009-0090025 (disclosed on Aug. 25, 2009, Title of invention: REDUCED SIZE DIGITAL DOORLOCK HAVING DUAL LOCKING HANDLE).

DISCLOSURE

Technical Problem

The present invention is directed to providing a door handle having an automatic sterilization function to disinfect pathogens including viruses.

In addition, the present invention is directed to providing a door handle having a handle withdrawal function for use only by authorized users.

In addition, the present invention is directed to providing a door handle capable of preventing disinfection light from spreading outward from the door handle in order to disinfect the door handle.

The objectives of the present invention are not limited to the above-mentioned objectives, and other objectives and advantages of the present invention which are not mentioned may be understood through the description below and will be more clearly understood from embodiments of the present invention. In addition, it may be easy to see that the objectives and advantages of the present invention may be realized by the means defined in the claims and their combinations.

Technical Solution

A door handle according to the present invention that addresses the problems described above is technically characterized by a sterilizer which emits germicidal light to sterilize pathogens of a handle part.

Specifically, in a state in which the handle part is positioned inside a housing, the light of the sterilizer is emitted to a doorpull provided in the handle part to sterilize the doorpull.

In addition, the present invention is technically characterized by blocking transmission of light, which sterilizes a handle part, to a user.

Specifically, the germicidal light is emitted to disinfect the handle part only in a state in which the handle part is accommodated inside a housing, and thus the germicidal light is blocked from being transmitted to the user. In addition, since a light guide part provided in the handle part blocks a gap between a second handle frame and the housing, the germicidal light is blocked from being transmitted to the user.

In addition, the present invention is technically characterized by a handle part which protrudes outward from a housing only in a case in which user authentication is complete.

Specifically, when a rotating guide is rotated by operation of a drive part, guide protrusions provided on the handle part move along a guide slot provided in the rotating guide and a first guide hole and a second guide hole provided in the housing, and thus the handle part protrudes outward from the housing so that a user may grasp the handle part.

In addition, a door handle according to the present invention may include at least any one of a housing, a drive part, a rotating guide, a handle part, a sterilizer, and a proximity detection sensor.

In addition, the housing may be fixed to a door and may have an inner space.

In addition, the drive part may be positioned inside the housing and may supply rotational power.

In addition, the rotating guide may be connected to the drive part to receive the rotational power and rotated inside the housing.

In addition, the handle part may be positioned inside the rotating guide, may protrude outward from the housing with forward rotation of the rotating guide, and may be accommodated inside the housing with reverse rotation of the rotating guide.

In addition, the sterilizer may be installed in the handle part and may emit germicidal light to disinfect the handle part.

In addition, the proximity detection sensor may be installed in the handle part and may detect whether there is an object inside a doorpull of the handle part protruding outward from the housing and transmit a measured value to a control unit.

In addition, the handle part may include a handle body installed inside the rotating guide and guide protrusions which extend outward from the handle body and of which movement is guided along holes provided in the rotating guide and the housing.

In addition, the handle body may include a first handle body having a side surface to which the guide protrusions are fixed. In addition, the handle body may include a second handle body connected to the first handle body and configured to protrude outward from the housing with rotation of the first handle body.

In addition, the second handle body may include a second handle frame having one side fixed to the first handle body and the other side spaced apart from the first handle body. In addition, the second handle body may include a doorpull formed as a concave groove part in a side surface of the second handle frame facing the first handle body.

In addition, the second handle body may include a second handle cover covering an open part of the second handle frame. In addition, the second handle body may include a lighting part positioned between the second handle cover and the second handle frame and configured to emit light toward the outside of the second handle cover.

In addition, the second handle body may include a light guide part installed in a ring shape along an outer circumference of the lighting part and configured to guide diffusion of the light emitted from the lighting part.

In addition, the sterilizer may be installed in the first handle body and may emit disinfection light toward the doorpull.

In addition, the housing may include a mounting part fixed to the door and configured to restrict movement of the drive part. In addition, the housing may include a case fixed to the mounting part and installed in a shape surrounding an outer circumference of the rotating guide. In addition, the housing may include a fixing guide fixed inside the case and including holes which guide movement of guide protrusions provided on the handle part.

In addition, the fixing guide may include a guide body formed in a cylindrical shape and having one side obliquely cut and the other side fixed to the mounting part. In addition, the fixing guide may include a first guide hole formed as a long spiral hole in the guide body and configured to guide the movement of the guide protrusion. In addition, the fixing guide may include a second guide hole formed as a long spiral hole in the guide body facing the first guide hole and configured to guide the movement of the guide protrusion.

In addition, the rotating guide may include a rotating guide body rotatably installed inside the housing and connected to the drive part to rotate. In addition, the rotating guide may include a guide slot formed as holes in the rotating guide body facing the first guide hole and the second guide hole provided inside the housing and configured to guide movement of guide protrusions provided in the handle part.

In addition, the rotating guide body may include a rotation base having a plate shape, a connect rib positioned at a rotation center of the rotation base and connected to the drive part, and a guide sidewall extending from the rotation base, positioned inside the housing, and having an inner side at which the guide slot is positioned.

In addition, the guide slot may include a first guide slot configured to guide the movement of the guide protrusion, which is provided at one side of the handle part, and installed at a position facing the first guide hole and a second guide slot configured to guide the movement of the guide protrusion provided at the other side of the handle part and installed at a position facing the second guide hole.

In addition, the first guide slot may include a first straight groove extending in a longitudinal direction of the housing and configured to guide the movement of the guide protrusion, a first upper groove formed as a groove having a shape bent from one side of the first straight groove, and a first lower groove formed as a groove having a shape bent from the other side of the first straight groove. In addition, the first upper groove and the first lower groove may extend in opposite directions from the first straight groove.

In addition, the second guide slot may include a second straight groove installed at a position facing the first straight groove and extending in the longitudinal direction of the housing, a second upper groove formed as a groove having a shape bent from one side of the second straight groove, and a second lower groove formed as a groove having a shape bent from the other side of the second straight groove. In addition, the second upper groove and the second lower groove may extend in opposite directions from the second straight groove.

In addition, the handle part may include guide protrusions protruding from two sides of the handle part. In addition, the housing may include a first guide hole and a second guide hole which guide forward and backward movement of the guide protrusions. In addition, the rotating guide may include a first guide slot facing the first guide hole and a second guide slot facing the second guide hole.

In addition, by forward rotation of the drive part, the rotating guide may be rotated, the guide protrusions inserted into the first guide slot and the second guide slot may be rotated forward along the first guide hole and the second guide hole, and the handle part may protrude outward from the housing.

In addition, by reverse rotation of the drive part, the rotating guide may be rotated, the guide protrusions inserted into the first guide slot and the second guide slot may be reversely rotated along the first guide hole and the second guide hole, and the handle part may be moved into the housing.

In addition, the first guide hole and the second guide hole may be formed as spiral holes inside the housing.

Advantageous Effects

A door handle according to the present invention can prevent an unauthorized user from coming into contact with a handle part to reduce contamination of the handle part and improve a security function because the handle part protrudes outward from a housing only in a state in which user authentication is completed.

In addition, according to the present invention, since a sterilizer emits germicidal light to sterilize a handle part, transmission of pathogens through the handle part can be blocked.

In addition, according to the present invention, since germicidal light is emitted to disinfect a handle part only in a state in which the handle part is accommodated in a housing, injury to a user can be prevented by blocking transmission of the germicidal light to the user.

In addition, according to the present invention, since a light guide part provided in a handle part blocks a gap between a second handle frame and a housing, germicidal light is prevented from being transmitted to a user, and thus injury to the user can be prevented.

In addition, according to the present invention, since a sterilization state of a handle part can be easily checked through operation of a lighting part provided in the handle part, ease of use can be improved.

In addition, according to the present invention, since a proximity detection sensor detects whether there is an object inside a doorpull of a handle part withdrawn outward from a housing and transmits a measured value to a control unit, operational stability can be improved by preventing a pinching accident.

In addition to the above-described effects, specific effects of the present invention will be described with the following description of specific embodiments for implementing the invention.

MODES OF THE INVENTION

Figure 1:
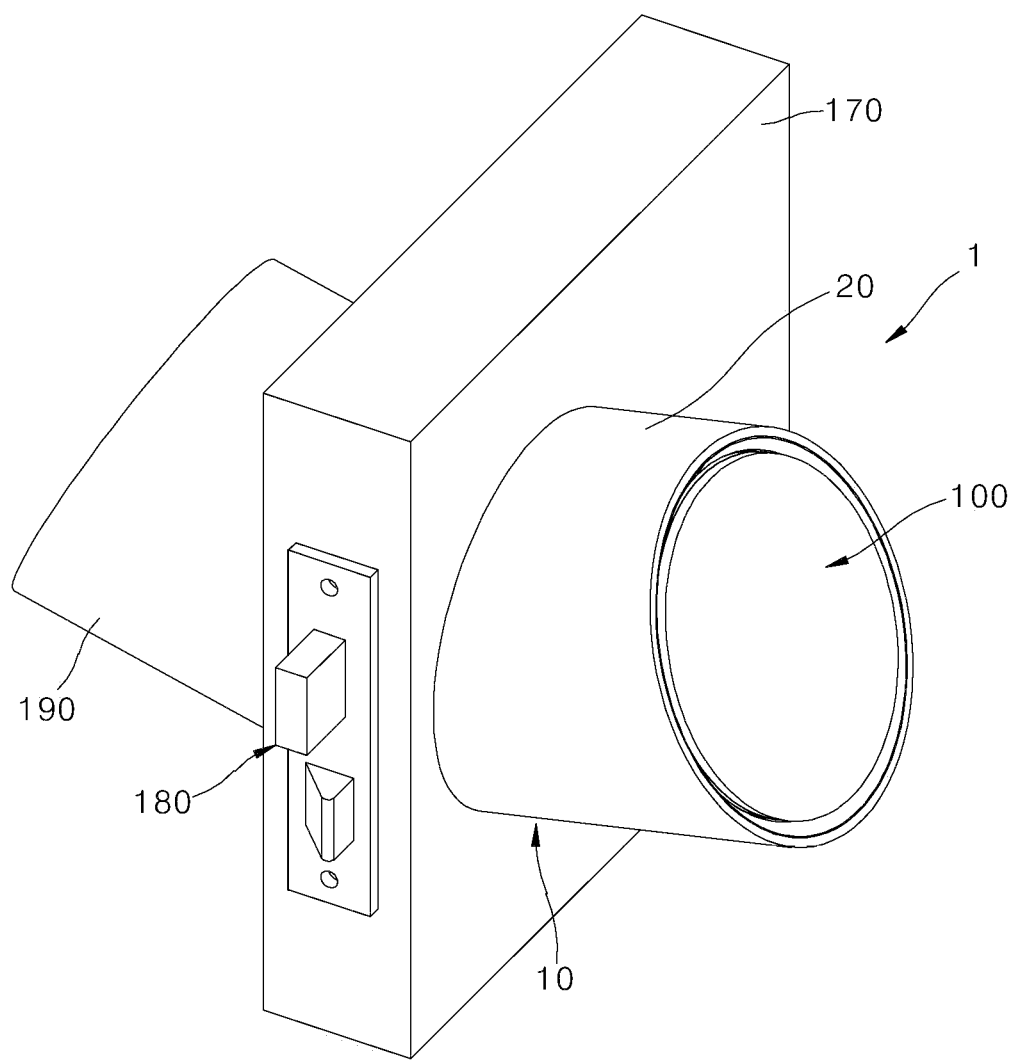
FIG. 1 is a perspective view illustrating a state in which a door handle is installed according to one embodiment of the present invention.

The above-described purposes, features, and advantages will be described in detail with reference to the accompanying drawings, and thus the technical spirit of the present invention may be easily executed by those skilled in the art. In describing the present invention, detailed descriptions of well-known technologies related to the present invention that unnecessarily obscure the gist of the invention will be omitted. Hereinafter, exemplary embodiments of the present invention will be described in detail with reference to the accompanying drawings. The same or similar elements are denoted by the same reference numerals in the drawings.

Figure 2:
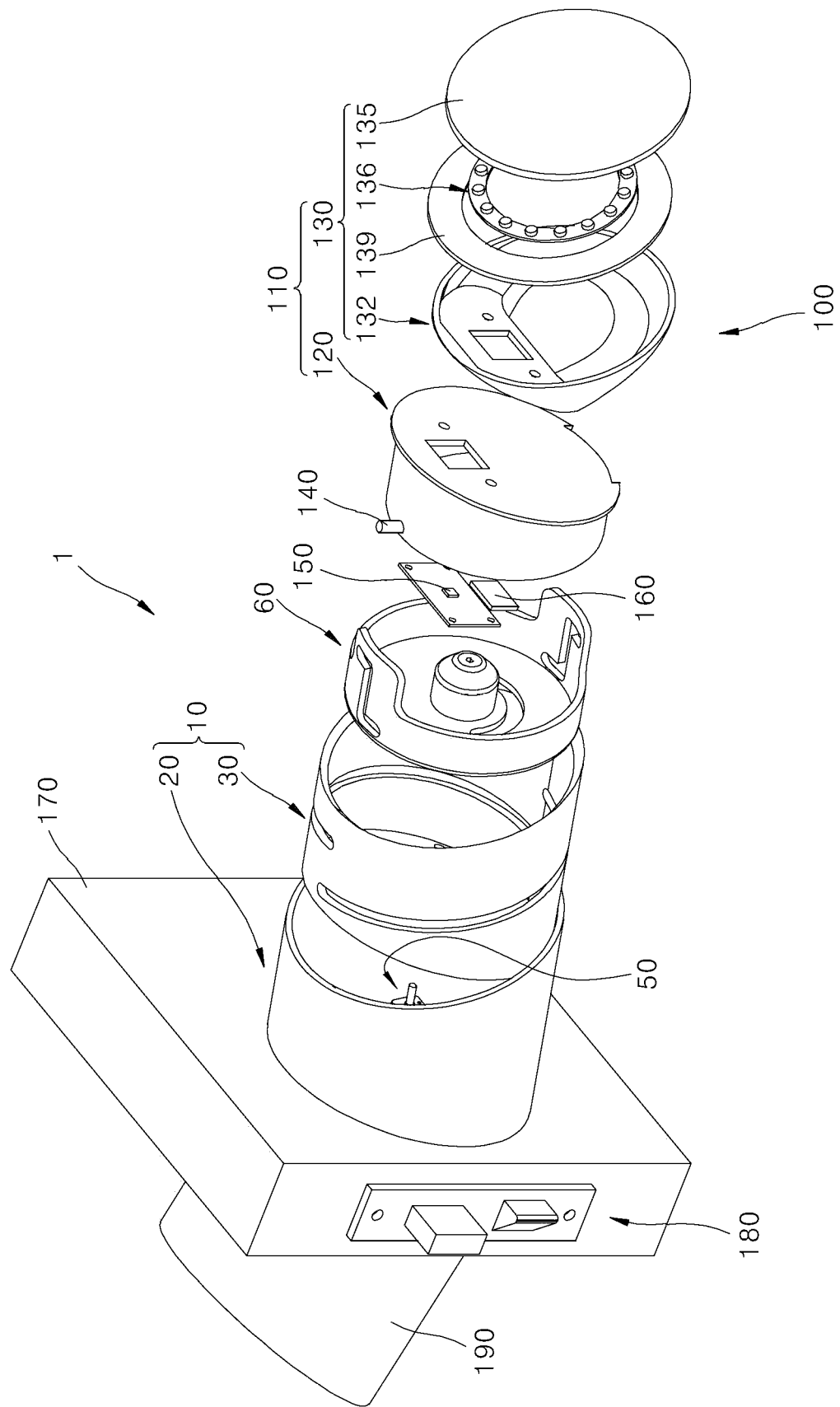
FIG. 2 is an exploded perspective view illustrating the door handle according to one embodiment of the present invention.

FIG. 1 is a perspective view illustrating a state in which a door handle 1 is installed according to one embodiment of the present invention, and FIG. 2 is an exploded perspective view illustrating the door handle 1 according to one embodiment of the present invention.

As illustrated in FIGS. 1 and 2, the door handle 1 according to one embodiment of the present invention may include at least any one of a housing 10, a drive part 50, a rotating guide 60, a handle part 100, a sterilizer 150, and a proximity detection sensor 160.

The door handle 1 according to the present invention may prevent contamination of the handle part 100 from many unspecified people and disinfect the handle part 100 in a relatively short time using an ultraviolet C (UV-C) sterilization function. By preventing the contamination of the handle part 100 from others, viruses or bacteria can be prevented from being brought into a house.

In addition, in the door handle 1 according to the present invention, the handle part 100 accommodated in the housing 10 rotates to protrude forward, and after being used, the handle part 100 rotates again to be accommodated inside of the housing 10. As described above, even when there are foreign materials in the handle part 100, due to a structure in which the handle part 100 operates while rotating, since the foreign materials may drop out of the handle part 100 with the rotation operation, contamination of the handle part 100 can be prevented.

In addition, since the proximity detection sensor is separately installed in the handle part 100 to detect whether a finger is pinched, an accident in which a user's finger is pinched in the moving handle part 100 can be prevented.

The housing 10 may be variously modified within the technical spirit of the housing 10 being fixed to the door 170 and having an inner space. The housing 10 having the predetermined space thereinside is fixed to the door 170 in a state in which movement is restricted, and guides movement of guide protrusions 140 provided on the handle part 100 with the rotating guide 60. In addition, the housing 10 may be formed of a single member or divided into a plurality of members as necessary. The housing 10 according to one embodiment of the present invention includes a case 20, a fixing guide 30, and a mounting part 40.

The housing 10 may include a first guide hole 34 and a second guide hole 36 which guide forward and backward movement of the guide protrusions 140. The first guide hole 34 and the second guide hole 36 may be installed in shapes opposite to each other, and spiral holes may be formed inside the housing 10.

The first guide hole 34 and the second guide hole 36 guide the guide protrusions 140 to rotate 180 degrees. In the present invention, a driving motor 52 operates for a set time and rotates the handle part 100 including the guide protrusions 140 at an angle of 180 degrees. The set time for operating the driving motor 52 is set in consideration of the time it takes the handle part 100 to rotate 180 degrees. Since a case in which the handle part 100 rotates less than 180 degrees may occur, an operating time of the driving motor 52 is set by adding a float time to the time it takes the handle part 100 to rotate 180 degrees. Accordingly, the driving motor 52 operates for the time it takes the handle part 100 to rotate 190 degrees. Both of the rotating guide 60 and the handle part 100 are rotated by the operation of the driving motor 52, and the guide protrusions 140 of the handle part 100 are hooked on the first guide hole 34 and the second guide hole 36 which guide only rotation of 180 degrees to restrict the rotation thereof, and only the rotating guide 60 further moves as much as a length corresponding to first and second upper grooves 82 and 92 and first and lower grooves 86 and 96.

With the above operation, the handle part 100 rotates 180 degrees forward to move forward or rotates 180 degrees in reverse to move backward so that operation of backward movement is precisely performed, and thus an effect of improving the operational reliability of the device can be obtained.

Meanwhile, when a separate device, such as an encoder, is added to the driving motor 52, or a servo motor which precisely controls a rotation angle is used, the driving motor 52 may be variously changed to operate only while the handle part 100 rotates 180 degrees, or the like.

Figure 5:
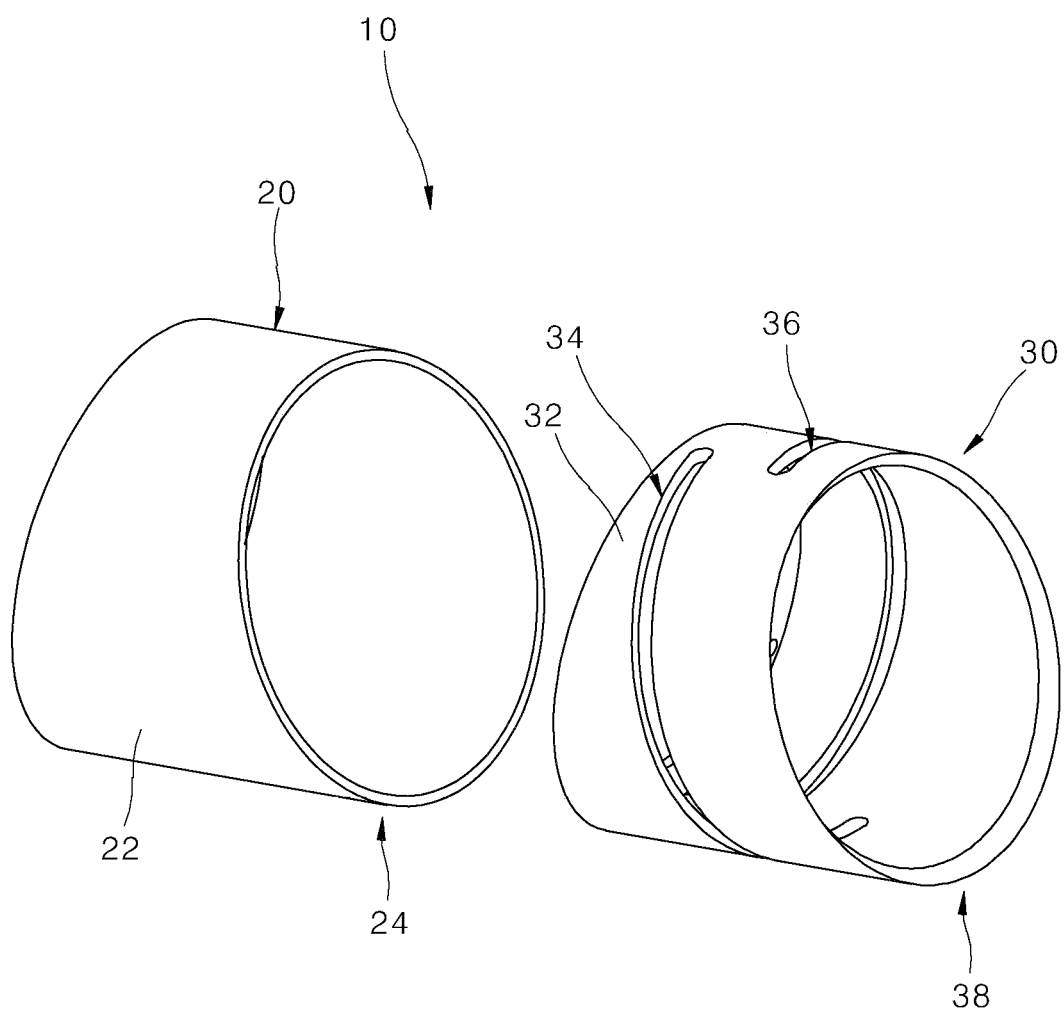
FIG. 5 is a perspective view illustrating a case and a fixing guide according to one embodiment of the present invention.

FIG. 5 is a perspective view illustrating the case 20 and the fixing guide 30 according to one embodiment of the present invention.

As illustrated in FIGS. 2 and 5, the case 20 is fixed to at least any one of the door 170 and the mounting part 40 and is installed in a shape surrounding an outer circumference of the rotating guide 60. The case 20 according to one embodiment of the present invention may include a case body 22 fixed to at least any one of the door 170 and the mounting part 40 and formed in a circular pipe shape and a case entrance 24 which is diagonally open at one side of the case body 22.

The case body 22 may be installed to be inclined upward. One side of the case body 22 is fixed to the door 170, and the open case entrance 24 is provided at the other side thereof.

A lower side of the case body 22 is obliquely installed to form a set angle A with respect to a virtual line extending horizontally. The set angle A is an acute angle, and preferably has a value in the range of 5 to 15 degrees. Accordingly, since the case body 22 is installed to be inclined upward, and the handle part 100 protruding outward from the case body 22 is also moved upward, a user may easily grasp a doorpull 134 provided in the handle part 100 and move the handle part 100.

The case entrance 24 is formed by obliquely cutting an entrance of the case body 22 in an inclined direction downward. A second handle cover 135 of the handle part 100 accommodated inside the case 20 may also be inclined at the same angle as the case entrance 24 and may be accommodated inside the case 20.

The fixing guide 30 may be variously changed within the technical range of the fixing guide 30 being fixed inside the case 20 and having the holes having long hole shapes which guide movement of the guide protrusions 140 provided on the handle part 100. The fixing guide 30 according to one embodiment of the present invention may include a guide body 32, the first guide hole 34, the second guide hole 36, and a guide entrance 38.

One side of the guide body 32 may be obliquely cut, and the other side thereof may include the guide body 32 having a cylindrical shape fixed to the mounting part 40. The guide body 32 may be positioned inside the case body 22 and formed in the same shape as the case body 22. That is, the guide body 32 is formed in the cylindrical shape and is obliquely installed upward.

In addition, the guide entrance 38 which is obliquely cut is installed at one side of the guide body 32. Inclined angles of the guide entrance 38 and the case entrance 24 may be the same.

The first guide hole 34 is formed as a long spiral hole in the guide body 32 and guides movement of the guide protrusion 140. In addition, the second guide hole 36 is formed as a long spiral hole in the guide body 32, faces the first guide hole 34, and guides movement of the guide protrusion 140.

Figure 3:
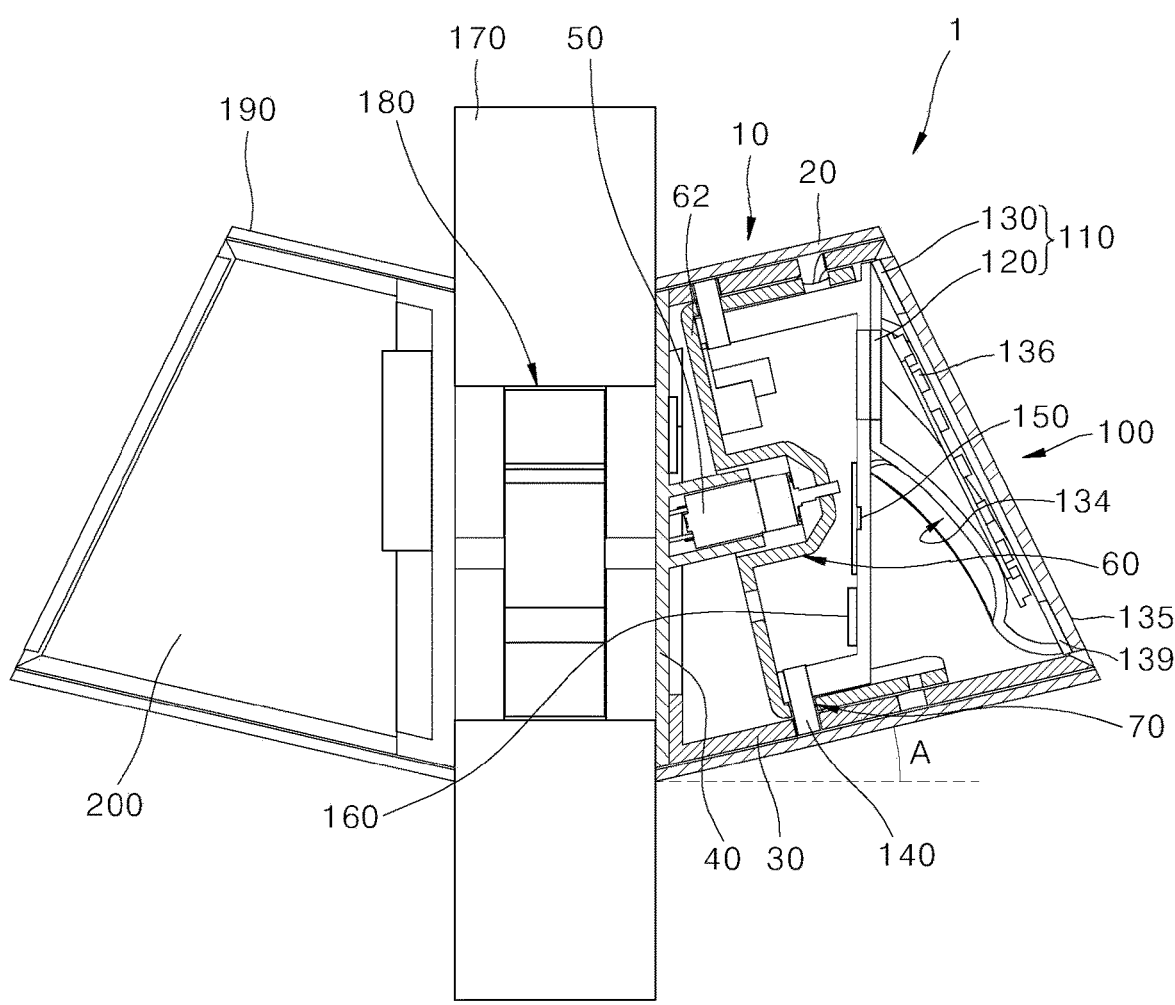
FIG. 3 is a cross-sectional view illustrating a state in which the door handle is installed according to one embodiment of the present invention.
Figure 6:
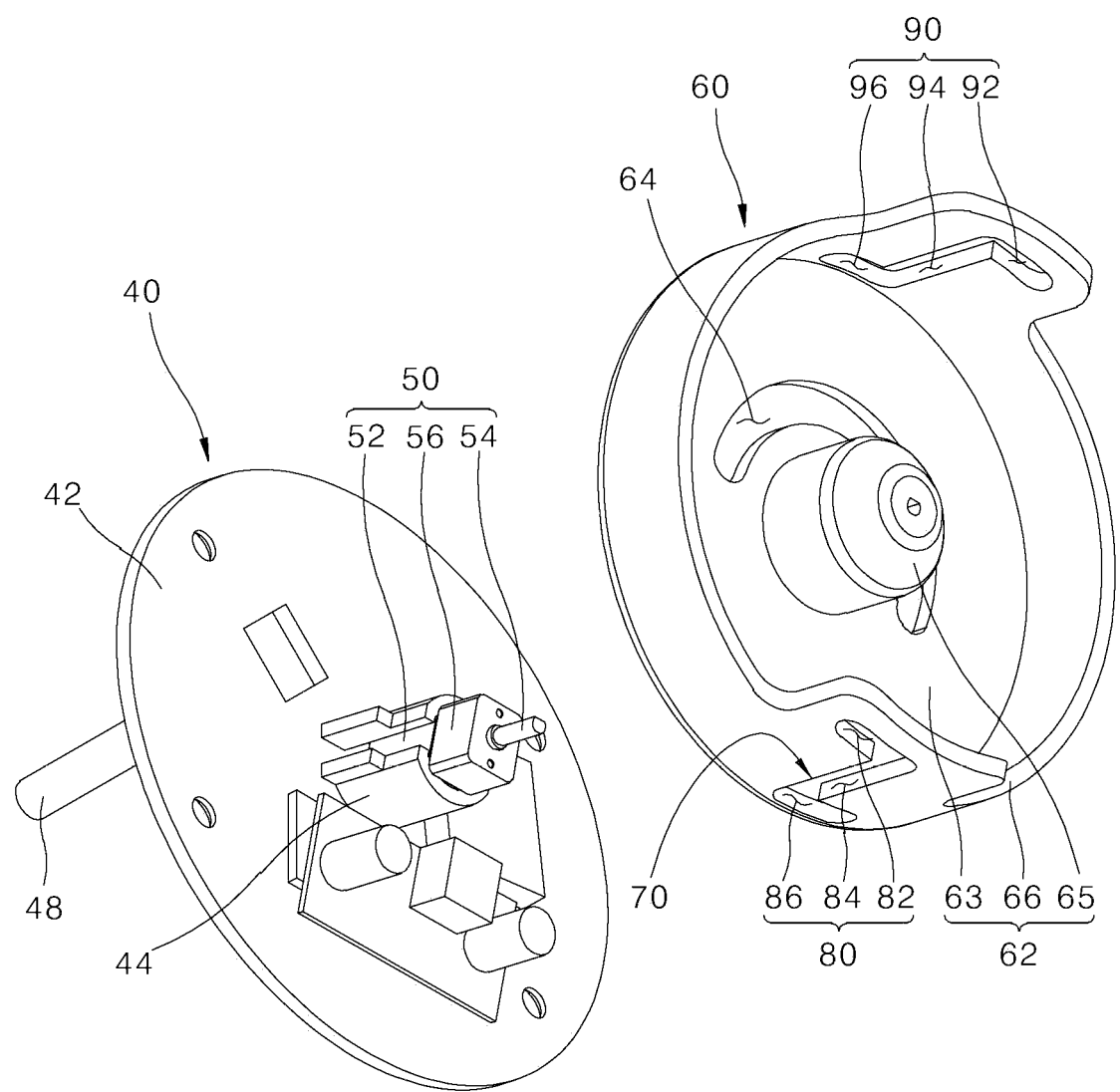
FIG. 6 is a perspective view illustrating a mounting part and a rotating guide according to one embodiment of the present invention.

FIG. 3 is a cross-sectional view illustrating a state in which the door handle 1 is installed according to one embodiment of the present invention, and FIG. 6 is a perspective view illustrating the mounting part 40 and the rotating guide 60 according to one embodiment of the present invention.

As illustrated in FIGS. 3 and 6, the mounting part 40 may be variously modified within the technical spirit of the mounting part 40 being fixed to the door 170 and restricting movement of the drive part 50. The mounting part 40 according to one embodiment of the present invention may include a base member 42, a motor bracket 44, and a mounting column 48.

The base member 42 is in contact with an outer side of the door 170 and has a plate shape, and the fixing guide 30 may be fixed to the base member 42. The base member 42 according to one embodiment of the present invention may be formed in a disc shape, and the shape may be changed to any shape as necessary.

The motor bracket 44 protruding forward from the base member 42 supports the drive part 50. Since the housing 10 is installed to be inclined at the set angle A, the motor bracket 44 is also installed to be inclined upward to support the driving motor 52.

The mounting column 48 protruding backward from the base member 42 may extend to an inner side of the door 170 and, as necessary, may be connected to a power storage part 200 provided in an indoor handle 190. Accordingly, power of the power storage part 200 may be transmitted to the drive part 50 through a power cable installed inside the mounting column 48.

The drive part 50 is positioned in the predetermined space of the housing 10 and supplies a rotation force for rotating the rotating guide 60. The drive part 50 may be variously modified within the technical spirit of the drive part 50 being positioned inside the housing 10 and supplying rotational power. The drive part 50 according to one embodiment of the present invention may include the driving motor 52 which is fixed to the mounting part 40 provided in the housing 10 and generates rotational power and a deceleration device 56 which is connected to the driving motor 52, decreases a speed, and increases a torque. In addition, since an output shaft 54 protruding outward from the deceleration device 56 is connected to the rotating guide 60, the rotating guide 60 rotates with the output shaft 54.

The driving motor 52 is fixed to the motor bracket 44 provided in the mounting part 40, and the deceleration device 56 receives the rotational power of the driving motor 52 and transmits the power, of which a speed is reduced, to the output shaft 54.

The rotating guide 60 may be variously modified within the technical spirit of the rotating guide 60 being connected to the drive part 50, receiving the rotational power, rotating inside the housing 10, and guiding movement of the guide protrusions 140. The rotating guide 60 may include a first guide slot 80 facing the first guide hole 34 and a second guide slot 90 facing the second guide hole 36. The rotating guide 60 according to one embodiment of the present invention may include a rotating guide body 62 and a guide slot 70.

Figure 10:
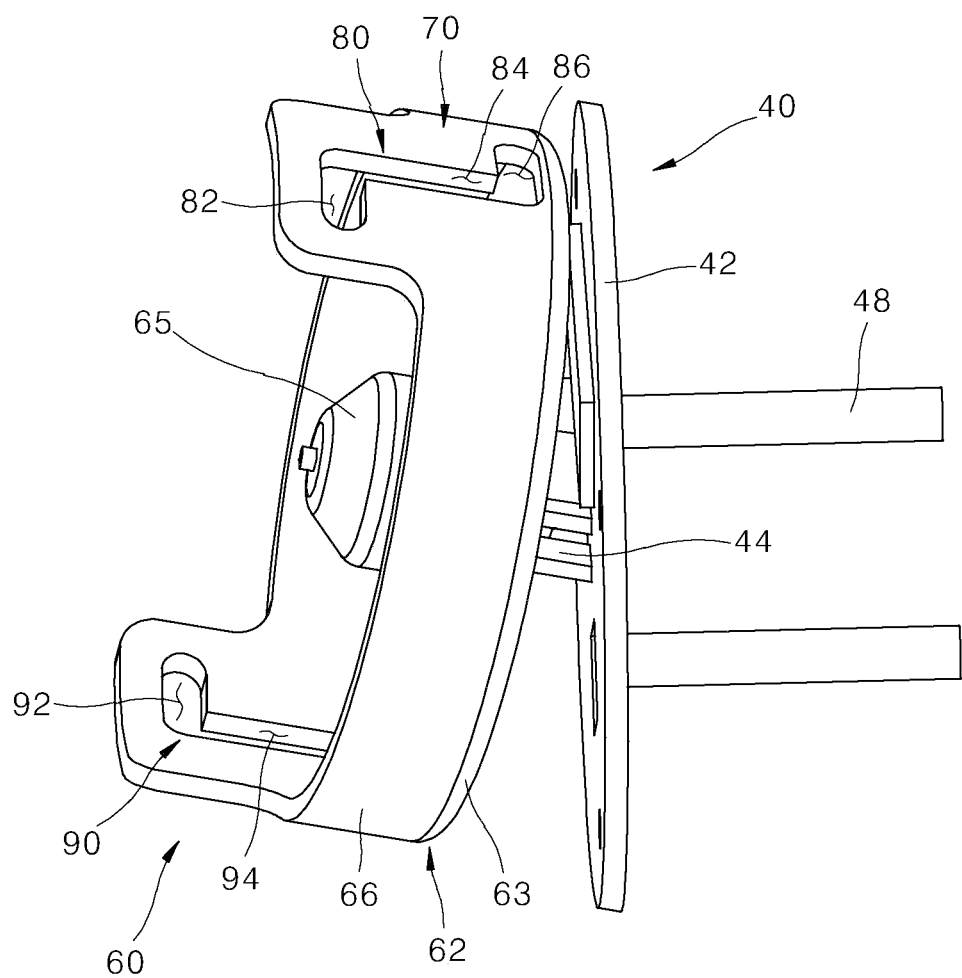
FIG. 10 is a perspective view illustrating the rotating guide according to one embodiment of the present invention.

FIG. 10 is a perspective view illustrating the rotating guide 60 according to one embodiment of the present invention.

As illustrated in FIGS. 6 and 10, the rotating guide body 62 may be variously modified within the technical spirit of the rotating guide body 62 being rotatably installed inside the housing 10 and connected to the drive part 50 to rotate. The rotating guide body 62 according to one embodiment of the present invention may include a rotation base 63, a connect rib 65, and a guide sidewall 66.

The rotation base 63 may be formed in a disc shape. The connect rib 65 is positioned at a rotation center of the rotation base 63 and is connected to the drive part 50. The connect rib 65 according to one embodiment of the present invention is positioned in a rotation center portion of the rotation base 63 and is installed in a convex shape protruding outward from the rotation base 63. The drive part 50 is positioned inside the connect rib 65, and the output shaft 54 of the drive part 50 is fixed to the connect rib 65.

A part of the rotation base 63 positioned outside the connect rib 65 is cut to form a connecting groove 64 which is a path through which the cable extends. The connecting groove 64 is formed as a hole along an arc shape in the rotation base 63. Accordingly, even when the rotating guide 60 rotates, the cable installed through the connecting groove 64 is not twisted or broken.

The guide sidewall 66 may be variously modified within the technical spirit of the guide sidewall 66 extending from the rotation base 63 and being positioned inside the housing 10 so that the guide slot 70 is positioned thereinside. The guide sidewall 66 according to one embodiment of the present invention is installed along an outer circumference of the rotation base 63 and extends on the rotation base 63 along an outer surface of the handle part 100.

The guide slot 70 may be variously modified within the technical spirit of the guide slot 70 being formed as hole in the rotating guide body 62 facing the first guide hole 34 and the second guide hole 36 provided inside the housing 10 and guiding movement of the guide protrusions 140 provided on the handle part 100. The guide slot 70 according to one embodiment of the present invention is formed as the first guide slot 80 and the second guide slot 90 formed inside the guide sidewall 66.

The first guide slot 80 guides movement of the guide protrusion 140 provided at one side of the handle part 100 and is installed at a position facing the first guide hole 34 of the fixing guide 30. The first guide slot 80 according to one embodiment of the present invention may include a first upper groove 82, a first straight groove 84, and a first lower groove 86.

The first straight groove 84 extends straightly in a longitudinal direction of the housing 10 and guides movement of the guide protrusion 140.

In addition, the first upper groove 82 is formed as a groove having a shape bent from one side of the first straight groove 84. The first upper groove 82 and the first straight groove 84 may be installed to form a right angle but are not limited thereto, and an angle formed by the first upper groove 82 and the first straight groove 84 may be changed within the range of an acute angle.

In addition, the first lower groove 86 is formed as a groove having a shape bent from the other side of the first straight groove 84. The first lower groove 86 and the first straight groove 84 may be installed to form a right angle but are not limited thereto, and an angle formed by the first lower groove 86 and the first straight groove 84 may be changed within the range of an acute angle.

In addition, the first upper groove 82 and the first lower groove 86 may extend in opposite directions from the first straight groove 84.

During a withdrawal operation of the handle part 100, the guide protrusions 140 of the handle part 100 rotate along the first straight groove 84 and the first guide hole 34 and move outward from the housing 10. When the driving motor 52 further rotates forward in a state in which the withdrawal operation of the handle part 100 is completed, since only the rotating guide 60 further rotates as much as a length in which the upper hole is formed in a state in which a rotation protrusion is hooked on one end portion of the first guide hole 34, transmission of an impact to the guide protrusion 140 may be reduced.

During a hidden operation of the handle part 100, the guide protrusion 140 of the handle part 100 rotates along the first straight groove 84 and the first guide hole 34 and moves inward from the housing 10. When the driving motor 52 further rotates in reverse in a state in which the hidden operation of the handle part 100 is completed, since only the rotating guide 60 further rotates as much as a length in which the first lower hole is formed in a state in which the rotation protrusion is hooked on the other end portion of the first guide hole 34, transmission of an impact to the guide protrusion 140 may be reduced.

As described above, when the drive part 50 is further operated to rotate the rotating guide 60 after operation of the handle part 100 is completed, because only the rotating guide 60 further rotates as much as the lengths of the first upper groove 82 and the first lower groove 86, damage to the guide protrusion 140 can be prevented.

The second guide slot 90 may be variously modified within the technical spirit of the second guide slot 90 guiding movement of the guide protrusion 140 provided on the other side of the handle part 100 and being installed at a position facing the second guide hole 36. The second guide slot 90 according to one embodiment of the present invention may include a second upper groove 92, a second straight groove 94, and a second lower groove 96.

The second straight groove 94 extends straightly in the longitudinal direction of the housing 10 and guides movement of the guide protrusion 140. In addition, the second straight groove 94 is installed in a position facing the first straight groove 84.

In addition, the second upper groove 92 is formed as a groove having a shape bent from one side of the second straight groove 94. The second upper groove 92 and the second straight groove 94 may be installed to form a right angle but are not limited thereto, and an angle formed by the second upper groove 92 and the second straight groove 94 may be changed within the range of an acute angle.

In addition, the second lower groove 96 is formed as a groove having a shape bent from the other side of the second straight groove 94. The second lower groove 96 and the second straight groove 94 may be installed to form a right angle but are not limited thereto, and an angle formed by the second lower groove 96 and the second straight groove 94 may be changed within the range of an acute angle.

In addition, the second upper groove 92 and the second lower groove 96 may extend in opposite directions from the second straight groove 94.

During the withdrawal operation of the handle part 100, the guide protrusion 140 of the handle part 100 rotates along the second straight groove 94 and the second guide hole 36 and moves outward from the housing 10. When the driving motor 52 further rotates forward in a state in which the withdrawal operation of the handle part 100 is completed, since only the rotating guide 60 further rotates as much as a length in which the second upper hole is formed in a state in which a rotation protrusion is hooked on one end portion of the second guide hole 36, transmission of an impact to the guide protrusions 140 can be reduced.

During the hidden operation of the handle part 100, the guide protrusion 140 of the handle part 100 rotates along the second straight groove 94 and the second guide hole 36 and moves inward from the housing 10. When the driving motor 52 further rotates in reverse in a state in which the hidden operation of the handle part 100 is completed, since only the rotating guide 60 further rotates as much as a length in which the second lower hole is formed in a state in which the rotation protrusion is hooked on the other end portion of the second guide hole 36, transmission of the impact to the guide protrusions 140 can be reduced.

As described above, when the drive part 50 is further operated to rotate the rotating guide 60 even after operation of the handle part 100 is completed, because only the rotating guide 60 further rotates as much as the lengths of the second upper groove 92 and the second lower groove 96, damage to the guide protrusion 140 can be prevented.

Figure 7:
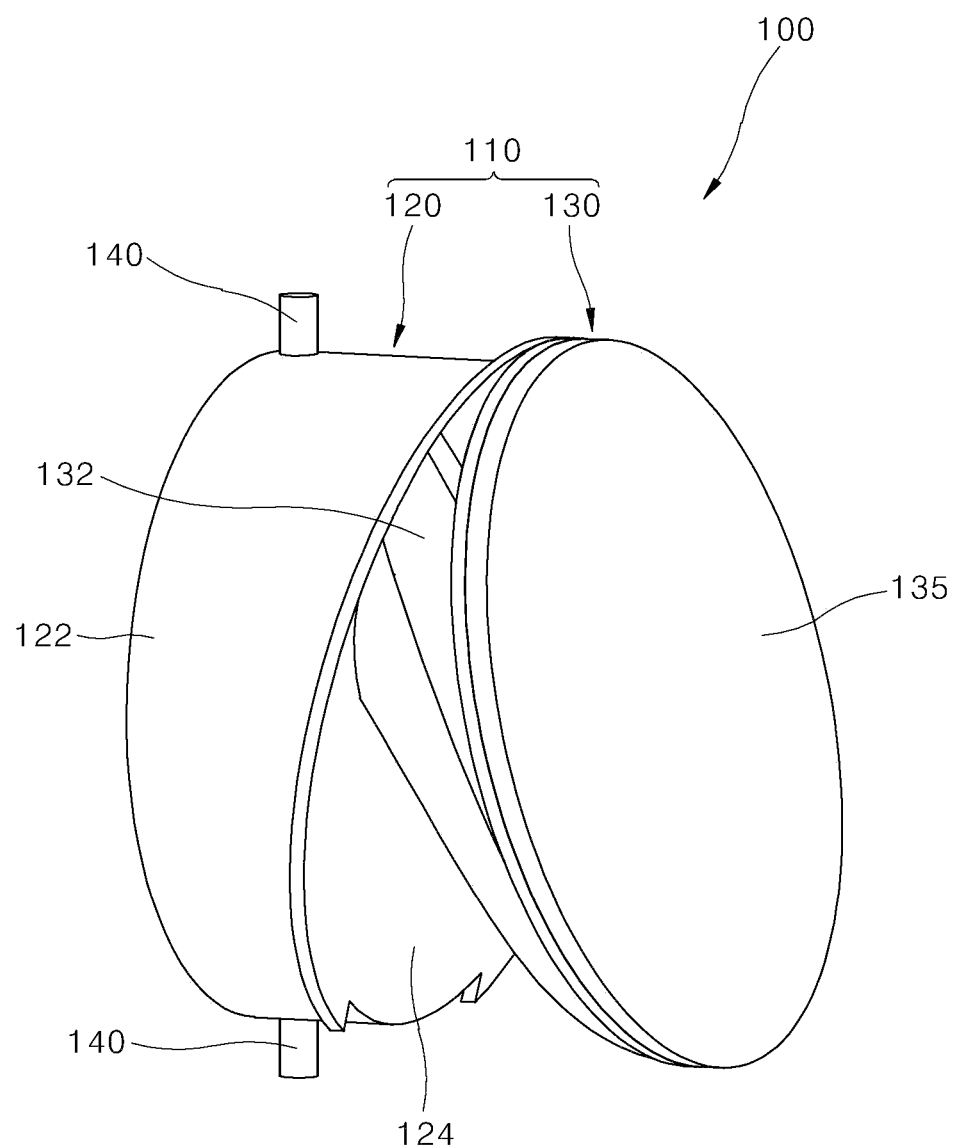
FIG. 7 is a perspective view illustrating a handle part according to one embodiment of the present invention.
Figure 8:
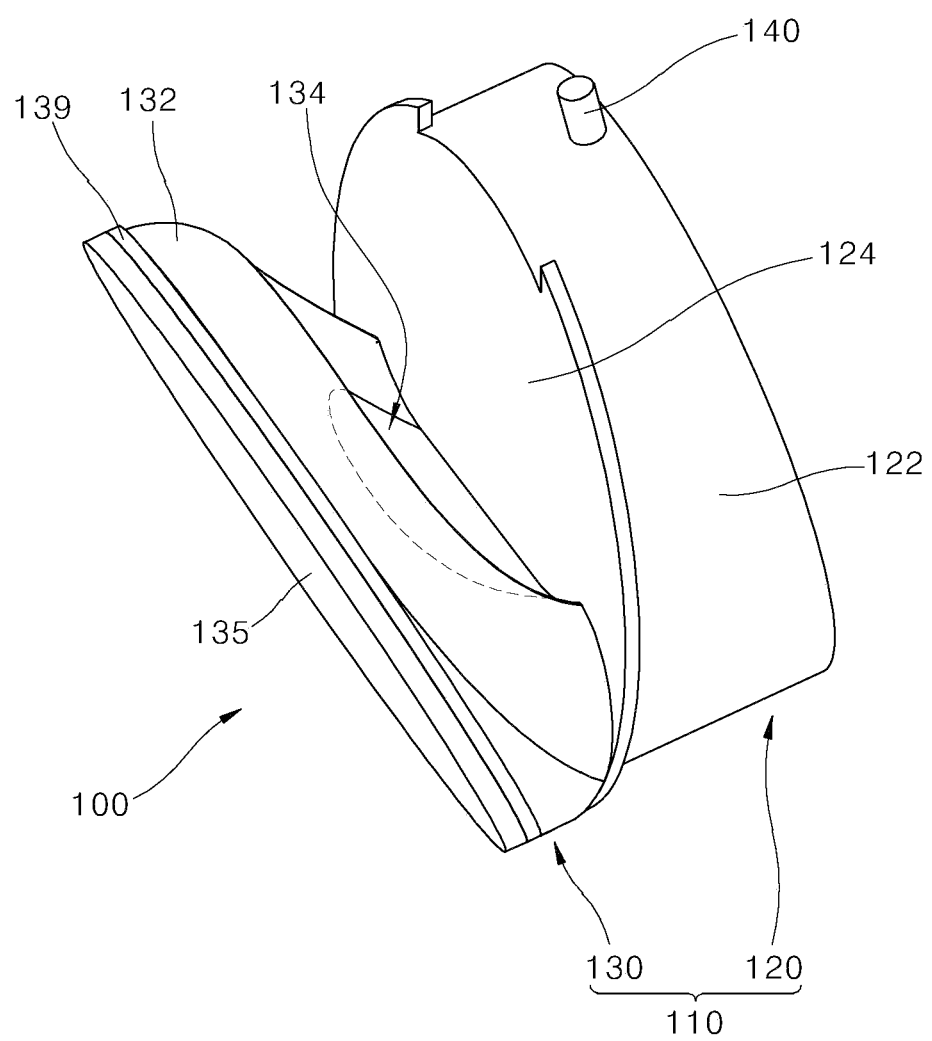
FIG. 8 is a perspective view illustrating a state in which a doorpull is provided in a second handle body according to one embodiment of the present invention.
Figure 9:
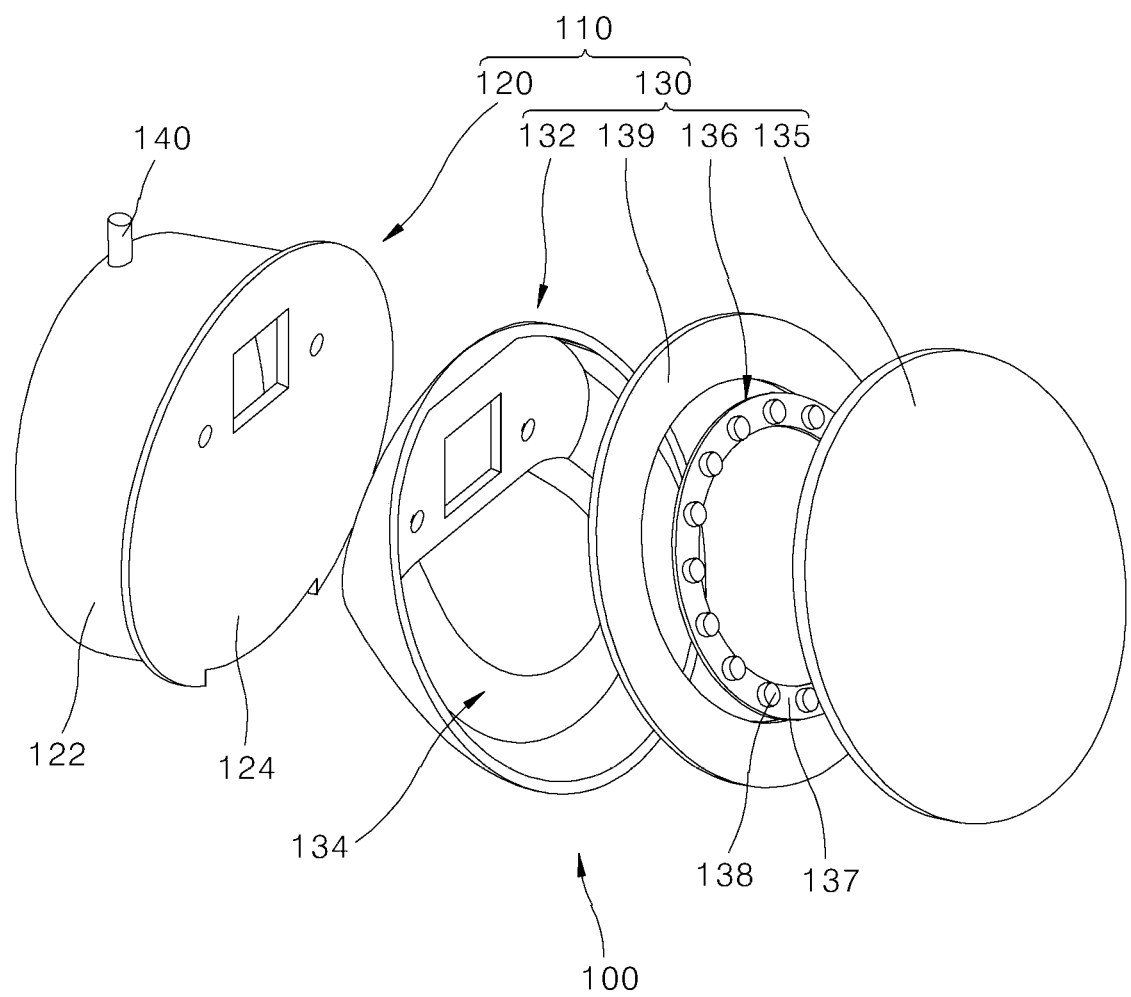
FIG. 9 is an exploded perspective view illustrating the handle part according to one embodiment of the present invention.

FIG. 7 is a perspective view illustrating the handle part 100 according to one embodiment of the present invention, FIG. 8 is a perspective view illustrating a state in which the doorpull 134 is provided in a second handle body 130 according to one embodiment of the present invention, and FIG. 9 is an exploded perspective view illustrating the handle part 100 according to one embodiment of the present invention.

As illustrated in FIGS. 7 to 9, the handle part 100 may be variously modified within the technical spirit of the handle part 100 being positioned inside the rotating guide 60, protruding outward from the housing 10 with forward rotation of the rotating guide 60, and being accommodated inside the housing 10 with reverse rotation of the rotating guide 60. The handle part 100 is positioned inside the rotating guide 60 and moves in the forward/reverse direction of the housing 10 by the forward/reverse rotation of the rotating guide 60.

A handle body 110 may be installed inside the rotating guide 60 and formed in a shape protruding outward from the housing 10 to be easily grasped by the user during user authentication. The handle body 110 according to one embodiment of the present invention may include a first handle body 120 and a second handle body 130.

The guide protrusions 140 are fixed to a side surface of the first handle body 120 and are positioned inside the rotating guide 60. A first handle frame 122 is installed in a shape surrounding the connect rib 65 of the rotating guide 60. The first handle frame 122 according to one embodiment of the present invention has a shape in which two sides are open, one side thereof is installed toward the rotation base 63 of the rotating guide 60, and the other side is installed toward the second handle body 130. The other side of the first handle frame 122 formed in a cylindrical shape may be obliquely cut to form an inclined shape.

The other side of the first handle frame 122 is covered by a first handle cover 124. The first handle cover 124 has a plate shape, and a path through which the cable extends is provided in a portion of the first handle cover 124 in contact with the second handle body 130.

The second handle body 130 may be variously modified within the technical spirit of the second handle body 130 being connected to the first handle body 120 and protruding outward from the housing 10 with rotation of the first handle body 120. A space into which a user's hand is inserted is provided between the first handle body 120 and the second handle body 130.

The second handle body 130 according to one embodiment of the present invention may include a second handle frame 132, the doorpull 134, the second handle cover 135, a lighting part 136, and a light guide part 139.

Since one side of the second handle frame 132 is fixed to the first handle body 120, and the other side of the second handle frame 132 is spaced apart from the first handle body 120, the space into which the user's finger is inserted is provided between the first handle frame 122 and the second handle frame 132. One side of the second handle frame 132 according to one embodiment of the present invention is fixed to the first handle body 120, and the other side thereof extends outward from the housing 10. A cross-sectional area of one side of the second handle frame 132 is formed to be small and fixed to the first handle cover 124, and a cross-sectional area of the other side of the second handle frame 132 gradually increases and has an open shape.

The doorpull 134 is formed as a concave groove part in a side surface of the second handle frame 132 facing the first handle body 120. Accordingly, in a state in which the handle part 100 is withdrawn outward from the housing 10, the user's finger moves through the space provided between the first handle body 120 and the second handle body 130, then grasps the doorpull 134, and pulls the handle part 100 to open the door 170.

The second handle cover 135 may be variously modified within the technical spirit of the second handle cover 135 covering an open part of the second handle frame 132. The second handle cover 135 according to one embodiment of the present invention may have a disc shape and may be formed of a light-transmitting material as necessary. Alternatively, only a part of the second handle cover 135 may be formed of a light-transmitting material and the rest may be formed of a material through which light does not pass.

The lighting part 136 may be variously modified within the technical spirit of the lighting part 136 being positioned between the second handle cover 135 and the second handle frame 132 and emitting light toward the outside of the second handle cover 135. The lighting part 136 according to one embodiment of the present invention may include a lighting substrate 137 and light source members 138.

In the present invention, since a sterilization state of the handle part 100 may be easily checked by operation of the lighting part 136 provided in the handle part 100, ease of use can be improved. For example, the handle part 100 may be variously modified such that, when the handle part 100 is disinfected, a color of the lighting part 136 is red, and when the handle part 100 is in a hidden mode, a color of the lighting part 136 may be changed to green, or the like.

The lighting substrate 137 is a substrate extending in a circumferential shape and is installed in a ring shape. A plurality of light source members 138 are installed along the lighting substrate 137. The light source members 138 may include light emitting diodes (LEDs).

The light guide part 139 is installed in a ring shape along an outer circumference of the lighting part 136 and guides diffusion of light emitted from the lighting part 136. The light guide part 139 has a plate shape installed along the circumferential shape and may be formed of a light-transmitting material as necessary.

Light generated from the lighting part 136 may be diffused toward an edge of the second handle cover 135 through the light guide part 139. Accordingly, since the light of the lighting part 136 is transmitted to the outside through an outer side of the edge of the second handle cover 135, an interior effect can be improved.

Meanwhile, the light guide part 139 may block germicidal light of the sterilizer 150, which will be described below, from leaking outward from the housing 10. Since the light guide part 139 blocks a gap between the fixing guide 30 and the second handle frame 132 provided in the housing 10, the light guide part 139 prevents a phenomenon in which the germicidal light emitted to sterilize the second handle frame 132 leaks between the fixing guide 30 and the second handle frame 132. Since the light guide part 139 provided in the handle part 100 blocks a gap between the second handle frame 132 and the housing 10, the germicidal light may be prevented from being transmitted to the user to prevent injury to the user.

Since the germicidal light is emitted and disinfects the handle part 100 only in a state in which the handle part 100 is accommodated inside the housing 10, the germicidal light is primarily blocked from being transmitted to the user. In addition, since the light guide part 139 blocks the gap between the second handle frame 132 and the fixing guide 30, the light which sterilizes the handle part 100 is secondarily blocked from being transmitted to the user.

Figure 11:
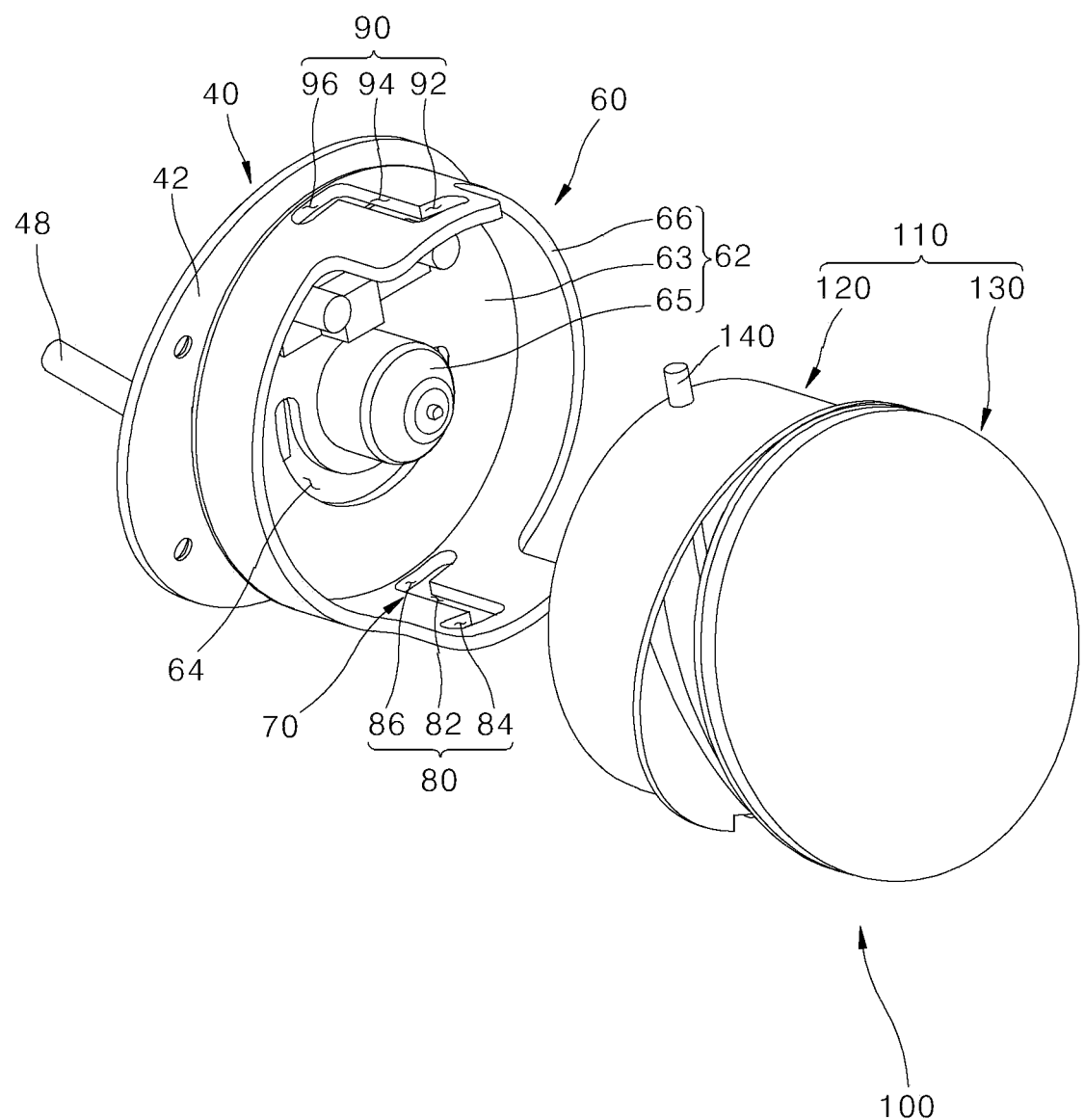
FIG. 11 is a perspective view illustrating a state in which the handle part is separated from the rotating guide according to one embodiment of the present invention.
Figure 12:
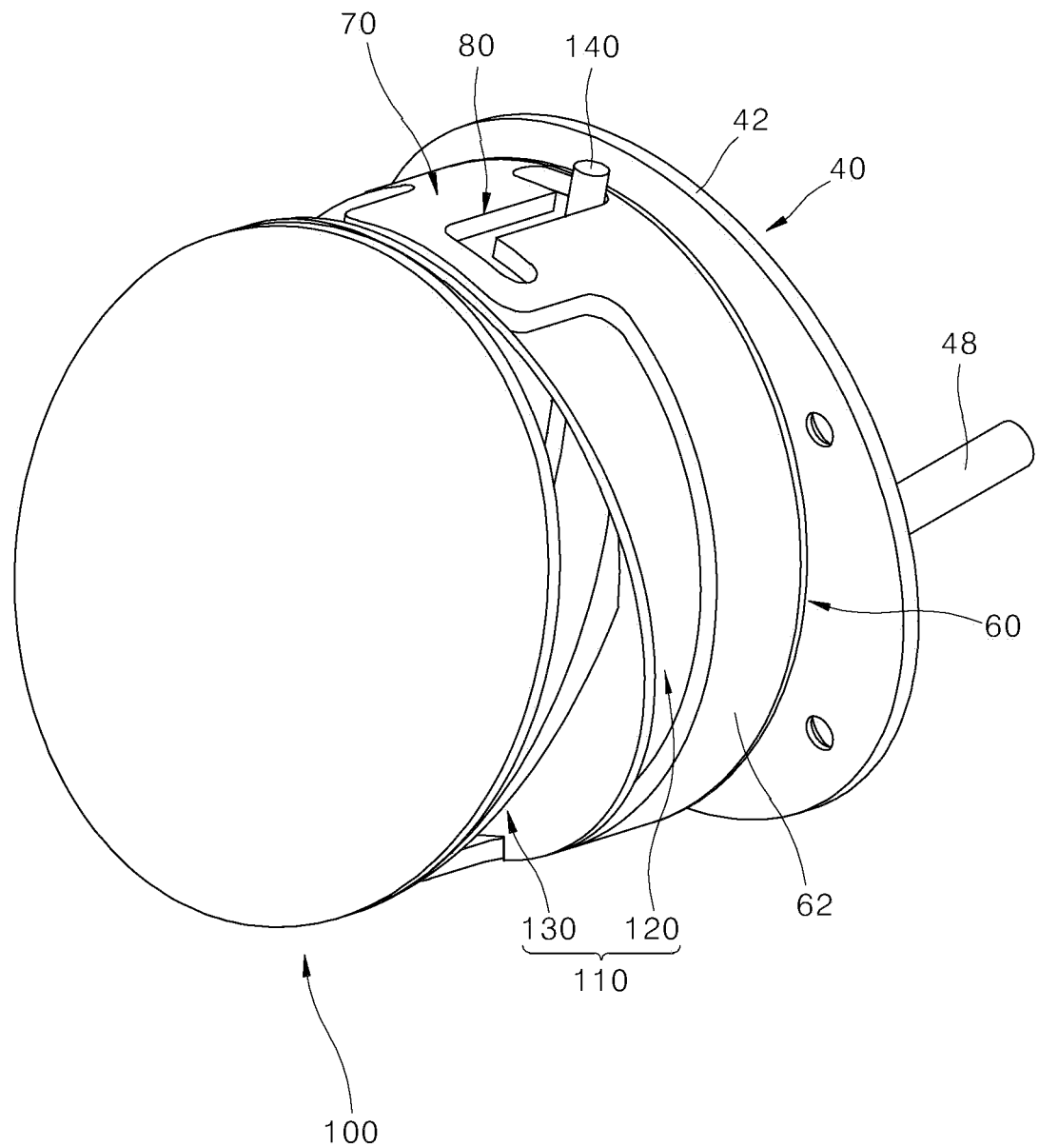
FIG. 12 is a perspective view illustrating a state in which the handle part is coupled to the rotating guide according to one embodiment of the present invention.

FIG. 11 is a perspective view illustrating a state in which the handle part 100 is separated from the rotating guide 60 according to one embodiment of the present invention, and FIG. 12 is a perspective view illustrating a state in which the handle part 100 is coupled to the rotating guide 60 according to one embodiment of the present invention.

As illustrated in FIGS. 11 and 12, the guide protrusions 140 protrude from two sides of the handle body 110, and movement thereof is guided by the fixing guide 30 and the rotating guide 60. The guide protrusions 140 are installed at intervals of 180 degrees and each formed in a circular column shape. The movement of the guide protrusions 140 is guided by the holes provided in the rotating guide 60 and the housing 10.

The guide protrusion 140 at one side is positioned in the first guide hole 34 through the first guide slot 80, and the guide protrusion 140 at the other side is positioned in the second guide hole 36 through the second guide slot 90. Accordingly, the handle body 110 is stably rotated when there are two guide protrusions 140 compared to when there is one guide protrusion 140.

Figure 4:
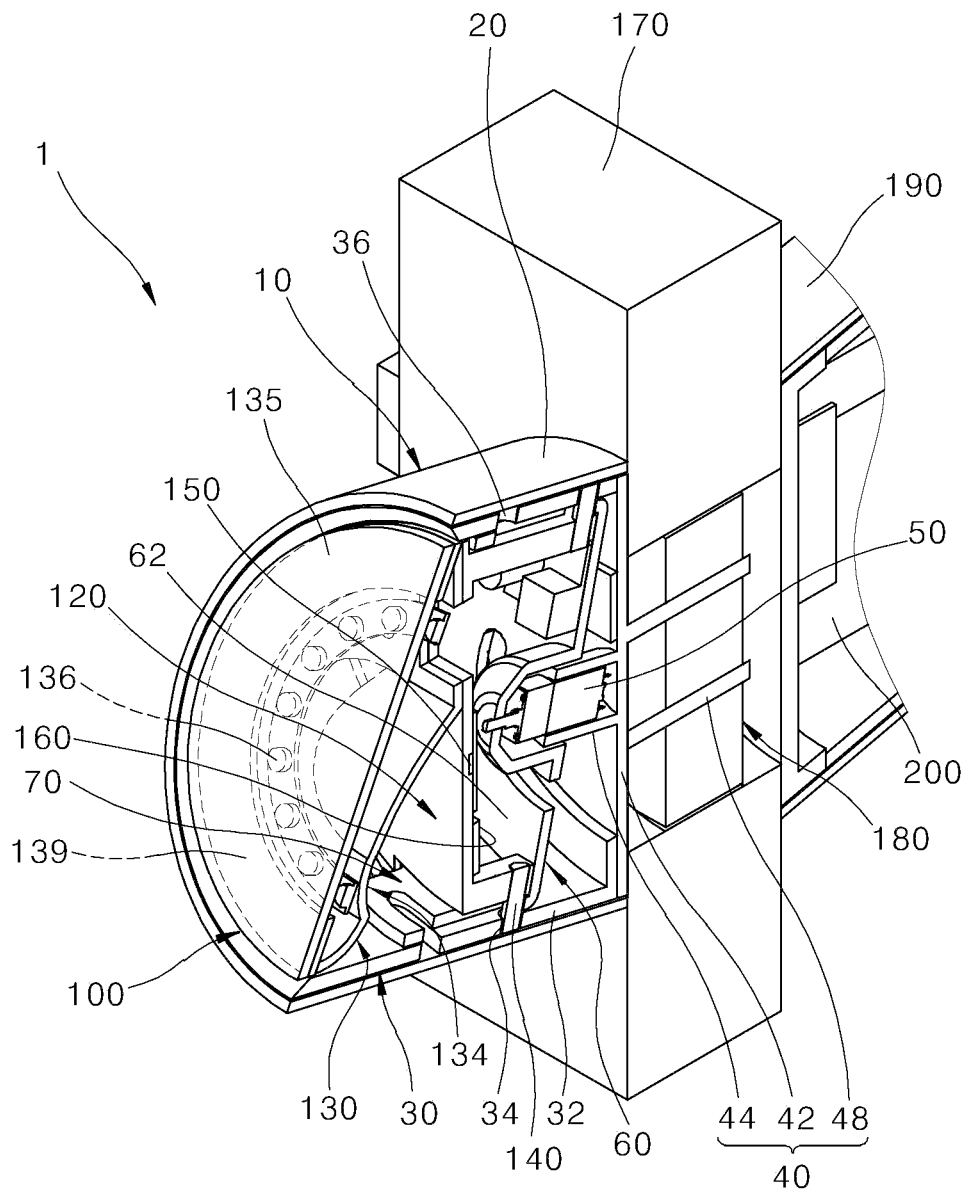
FIG. 4 is a partially cut perspective view illustrating the door handle according to one embodiment of the present invention.
Figure 13:
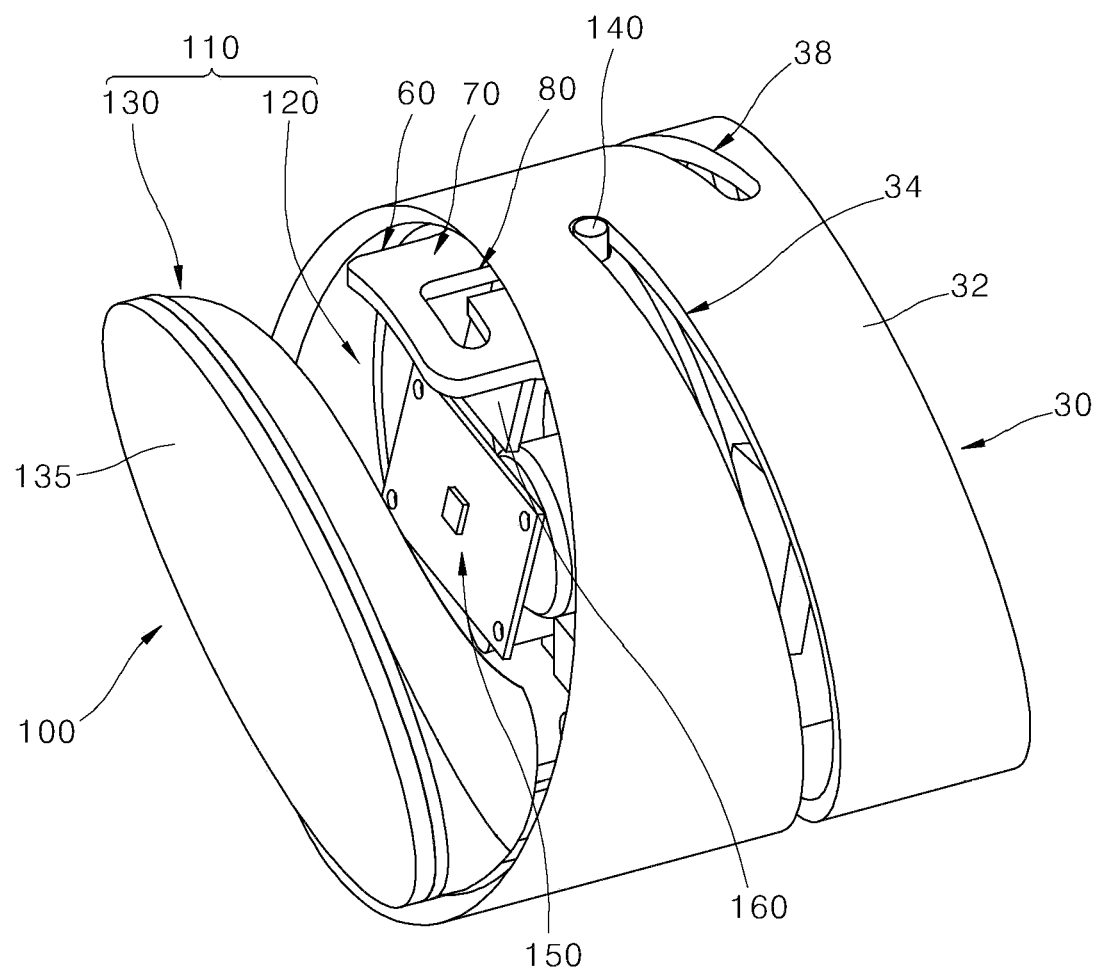
FIG. 13 is a perspective view illustrating a state in which the fixing guide is installed on an outer side of the rotating guide according to one embodiment of the present invention.

FIG. 4 is a partially cut perspective view illustrating the door handle 1 according to one embodiment of the present invention, and FIG. 13 is a perspective view illustrating a state in which the fixing guide 30 is installed outside the rotating guide 60 according to one embodiment of the present invention.

As illustrated in FIGS. 4 and 13, the guide protrusions 140 are inserted into the first guide hole 34 and the second guide hole 36 provided in the fixing guide 30. Accordingly, when the rotating guide 60 rotates, the guide protrusions 140 rotate while moving in the longitudinal direction of the housing 10.

Meanwhile, the sterilizer 150 may be variously modified within the technical spirit of the sterilizer 150 being installed in the handle part 100 and emitting germicidal light to disinfect the handle part 100. The sterilizer 150 according to one embodiment of the present invention may be installed in the handle body 110 and may emit disinfection light toward the doorpull 134.

In a state in which the handle part 100 is positioned inside the housing 10, germicidal light of the sterilizer 150 is emitted to the doorpull 134 provided in the handle part 100 to sterilize the doorpull 134. That is, since the germicidal light is emitted and disinfects the handle part 100 only in a state in which the handle part 100 is accommodated inside the housing 10, the germicidal light can be prevented from being transmitted to the user to prevent injury to the user. In addition, since the sterilizer 150 emits the germicidal light to sterilize the handle part 100, transmission of pathogens through the handle part 100 can be prevented.

The sterilizer 150 is installed inside the first handle body 120 and sterilizes the second handle body 130 including the doorpull 134 through the first handle cover 124.

The first handle cover 124 is formed of a light-transmitting material such as a transparent acrylic, and the sterilizer 150 may be fixed inside the first handle cover 124. The sterilizer 150 may disinfect the handle part 100 in a relatively short time using a UV-C LED which emits ultraviolet light having a wavelength in the range of 100 to 280 nm.

In addition, the proximity detection sensor 160 is installed in the handle part 100 and may detect whether there is an object inside the doorpull 134 of the handle part 100 protruding outward from the housing 10 and transmit a measured value to a control unit. Since the proximity detection sensor 160 is also installed inside the first handle cover 124, the proximity detection sensor 160 is not exposed from an exterior. The proximity detection sensor 160 measures whether there is an object such as the user's finger in the space formed between the first handle body 120 and the second handle body 130.

Accordingly, in an operation in which the handle part 100 tries to move into the housing 10 after the handle part 100 is used, when there is an object such as the user's finger between the first handle body 120 and the second handle body 130, the drive part 50 can be stopped to prevent a pinching accident.

Since the proximity detection sensor 160 detects whether there is an object inside the doorpull 134 of the handle part 100 withdrawn outward from the housing 10 and transmits a measured value to the control unit, a pinching accident can be prevented to improve operational stability.

The door handle 1 is installed outside the door 170, and the indoor handle 190 is installed inside the door 170. In the door handle 1, the handle part 100 is installed to be movable along the housing 10 so that only an authorized user may grasp the handle part 100. However, the indoor handle 190 may be formed to be grasped by the user always.

The power storage part 200 which supplies power to operate the drive part 50 may be installed inside the indoor handle 190. In addition, a locking device 180 capable of restricting movement of the door 170 is installed in the door 170. The locking device 180 may be unlocked by operation of the door handle 1 and variously modified so that locking is automatically released by a separately provided authentication device, or the like.

In addition, since the handle part 100 protrudes outward from the housing 10 only in a state in which user authentication is completed, the door handle 1 according to the present invention can reduce contamination of the handle part 100 and improve a security function by preventing an unauthorized user from coming into contact with the handle part 100.

Figure 19:
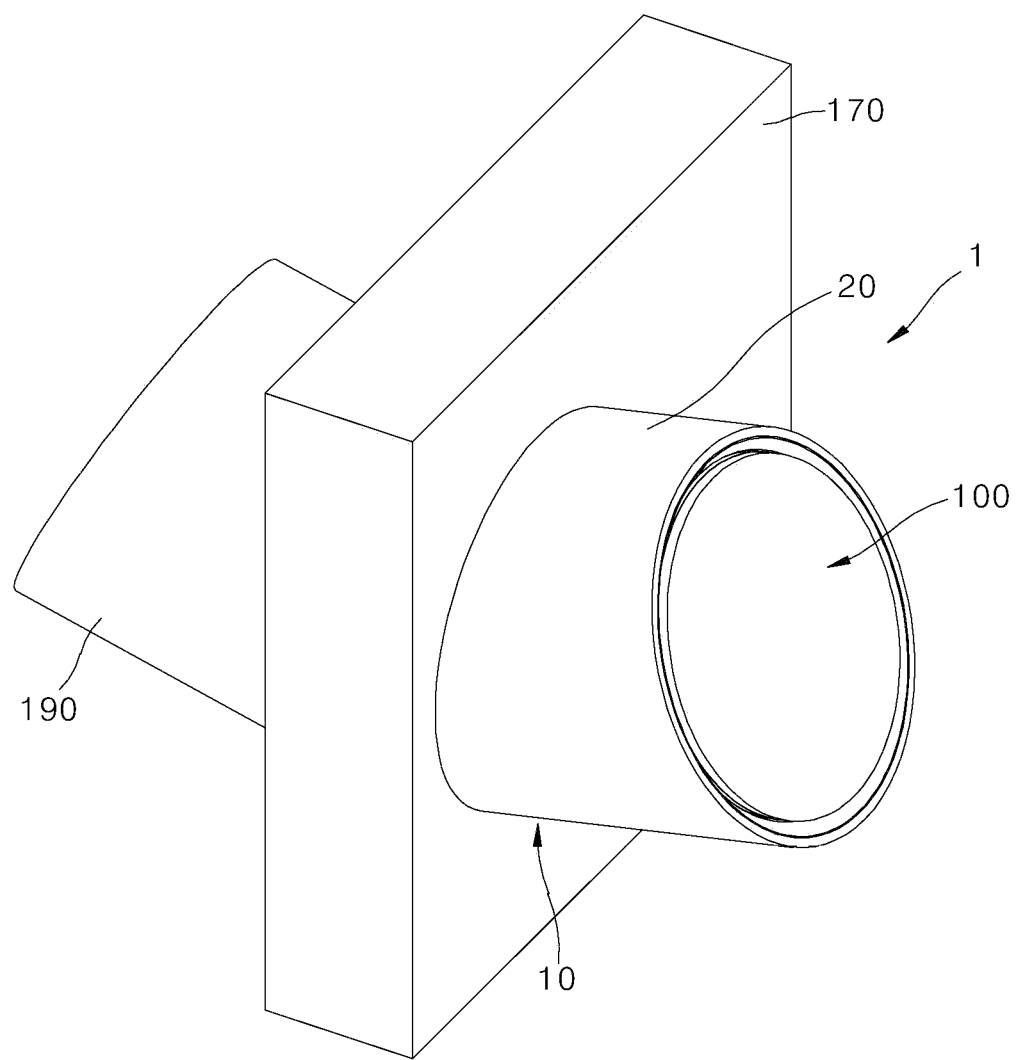
FIG. 19 is a perspective view illustrating a state in which the handle part is installed in a door according to one embodiment of the present invention.

FIG. 19 is a perspective view illustrating a state in which the handle part 100 is installed on the door 170 according to one embodiment of the present invention.

As illustrated in FIG. 19, a locking device which restricts movement of the door 170 may not be installed on the door 170 on which the door handle 1 according to one embodiment of the present invention is installed. In this case, a locking device which restricts movement of the door 170 is installed on a door frame (not shown) adjacent to the door 170, and a hook for hooking the locking device may be separately provided on the door 170.

Accordingly, in a state in which the door 170 is closed and faces the door frame, since the locking device installed on the door frame is operated and hooked on the door 170, movement of the door 170 can be restricted. In addition, the door 170 may be switched to a movable state by unlocking the locking device installed on the door frame, and the drive part 50 may operate so that the handle part 100 may protrude outward from the housing 10.

Meanwhile, the housing may be installed to be fixed inside the door 170 without protruding outward from the door 170. Accordingly, in a normal state in which there is no portion protruding outward from the door 170, the handle part 100 may protrude outward from the door 170 after user authentication is completed.

Alternatively, a structure corresponding to the first guide hole 34 and the second guide hole 36 for guiding movement of the guide protrusions 140 may be provided inside the door 170, and the door handle 1 in which a structure of the housing 10 is omitted may also be provided. In this case, the guide protrusions 140 may rotate along spiral holes provided inside the door 170 and perform forward and backward operations.

Hereinafter, an operation state of the door handle 1 according to one embodiment of the present invention will be described in detail with reference to the accompanying drawings.

Figure 14:
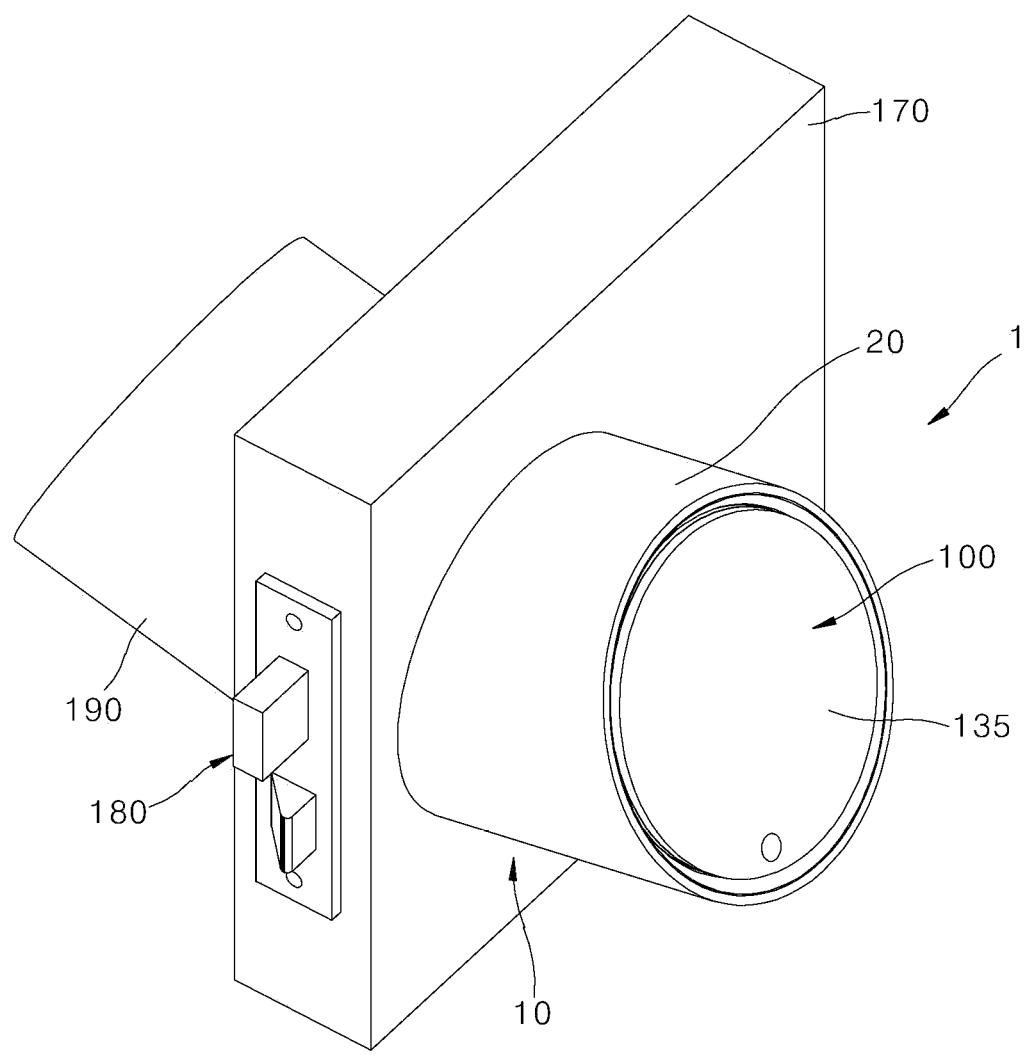
FIG. 14 is a perspective view illustrating a state in which the door handle waits in a standby mode according to one embodiment of the present invention.

FIG. 14 is a perspective view illustrating a state in which the door handle 1 waits in a standby mode according to one embodiment of the present invention. As illustrated in FIG. 14, the handle part 100 is positioned inside the housing 10, and only the second handle cover 135 is exposed to the outside. Since the case 20 has a cylindrical shape, and the second handle cover 135 is obliquely installed, an operation of grasping and moving the door handle 1 is difficult for an unauthorized user.

Figure 15:
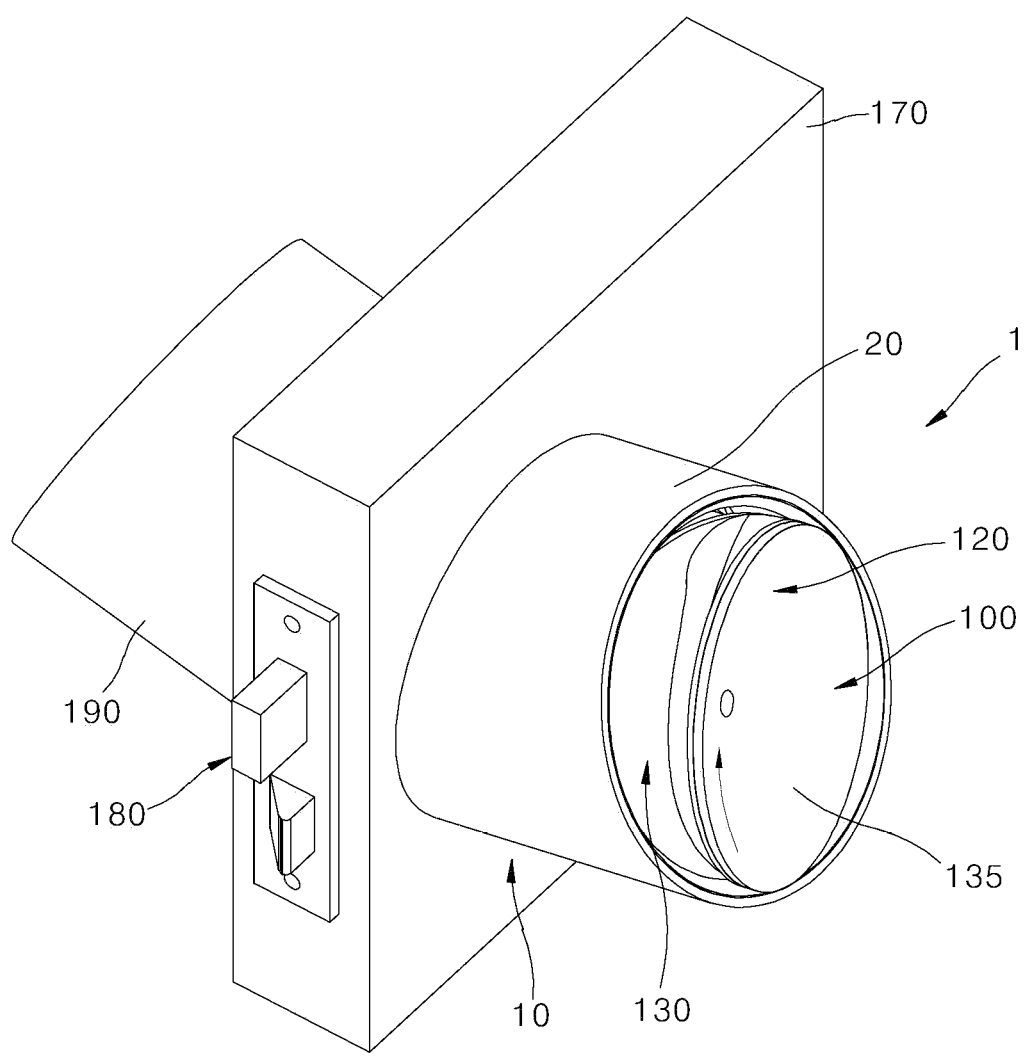
FIG. 15 is a perspective view illustrating a state in which the handle part rotates to protrude outward from a housing according to one embodiment of the present invention.

FIG. 15 is a perspective view illustrating a state in which the handle part 100 rotates to protrude outward from the housing 10 according to one embodiment of the present invention. As illustrated in FIG. 15, in a state in which the user's authentication is complete, the handle part 100 rotates forward to protrude outward from the case 20.

As illustrated in FIGS. 2 and 4, when the drive part 50 rotates the rotating guide 60, the guide protrusions 140 hooked on the guide slot 70 of the rotating guide 60 move along the first guide hole 34 and the second guide hole 36 provided in the fixing guide 30.

The guide protrusions 140 are moved by rotation of the guide slot 70 and moved forward to the outside of the housing 10 while spirally rotating along the first guide hole 34 and the second guide hole 36. Accordingly, the handle body 110 fixed to the guide protrusions 140 is also rotated with the guide protrusions 140 and moved outward from the housing 10.

Figure 16:
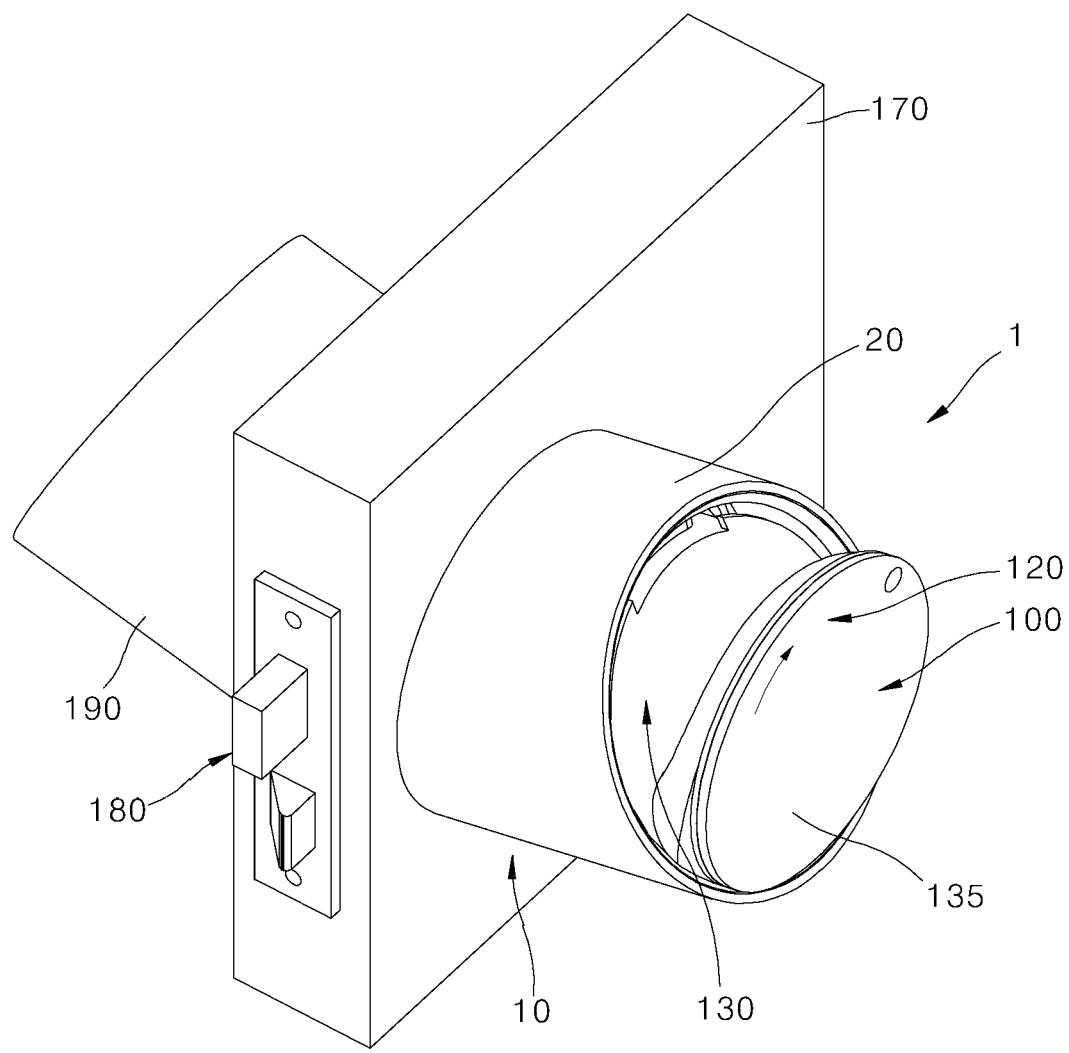
FIG. 16 is a perspective view illustrating a state in which the handle part is completely moved outward from the housing according to one embodiment of the present invention.

FIG. 16 is a perspective view illustrating a state in which the handle part 100 is completely moved outward from the housing 10 according to one embodiment of the present invention.

As illustrated in FIG. 16, 180-degree rotation of the handle part 100 is stopped in a state in which the handle part 100 protrudes outward from the housing 10. In addition, since the lighting part 136 operates so that the LED emits light, a signal indicating that the user can grasp the handle part 100 is sent.

Figure 17:
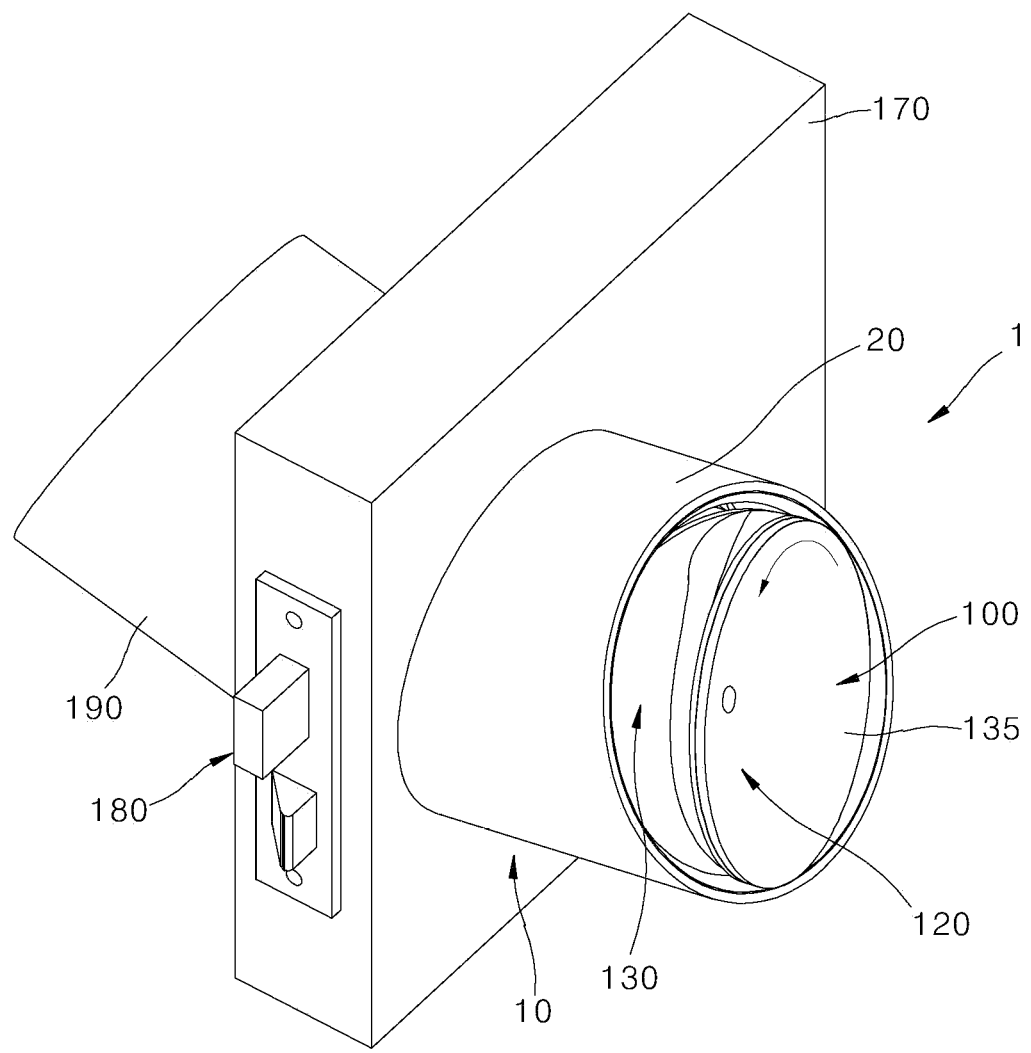
FIG. 17 is a perspective view illustrating a state in which the handle part rotates to move into the housing according to one embodiment of the present invention.

FIG. 17 is a perspective view illustrating a state in which the handle part 100 rotates to move into the housing 10 according to one embodiment of the present invention.

As illustrated in FIG. 17, after use of the handle part 100 is completed, the handle part 100 further rotates in reverse to move into the housing 10. The inward movement of the handle part 100 is performed in a reverse order of the outward movement of the handle part 100.

Figure 18:
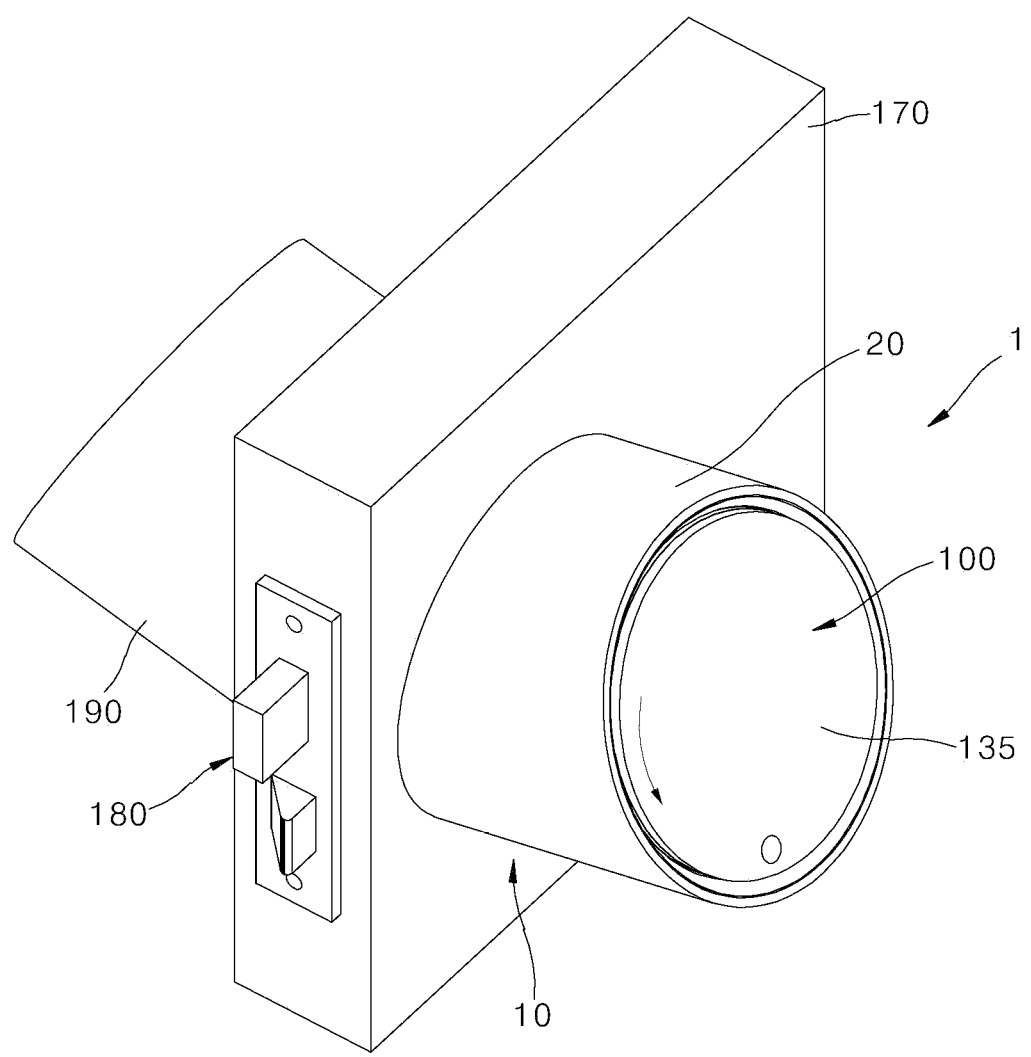
FIG. 18 is a perspective view illustrating a state in which the handle part is completely accommodated inside the housing according to one embodiment of the present invention.

FIG. 18 is a perspective view illustrating a state in which the handle part 100 is completely accommodated inside the housing 10 according to one embodiment of the present invention.

As illustrated in FIG. 18, in the hidden mode state in which the handle part 100 is completely accommodated inside the housing 10, the sterilizer 150 operates to emit germicidal light to the handle part 100 to disinfect the handle part 100.

As illustrated in FIGS. 2 to 4, in the door handle 1 according to the present invention, the handle part 100 protrudes outward from the housing 10 only in a state in which user authentication is completed. When the rotating guide 60 is rotated by operation of the drive part 50, since the guide protrusions 140 provided in the handle part 100 move along the guide slot 70 provided in the rotating guide 60 and the first guide hole 34 and the second guide hole 36 provided in the housing 10, the handle part 100 may protrude outward from the housing 10 and may be grasped by the user.

With forward rotation of the drive part 50, the rotating guide 60 may rotate forward, the guide protrusions 140 inserted into the first guide slot 80 and the second guide slot 90 may rotate forward along the first guide hole 34 and the second guide hole 36, and the handle part 100 may protrude outward from the housing 10.

In addition, with reverse rotation of the drive part 50, the rotating guide 60 may rotate, the guide protrusions 140 inserted into the first guide slot 80 and the second guide slot 90 may rotate in reverse along the first guide hole 34 and the second guide hole 36, and the handle part 100 may move into the housing 10.

As described above, since the handle part 100 is normally in the hidden mode in which the handle is accommodated inside the housing 10, an outsider may be essentially blocked from coming into contact with the handle part 100. In addition, even when an outsider with pathogens comes into contact with the handle part 100, the handle part 100 is sterilized using the UV-C so that the germs are not transmitted to others who use the handle part 100. Meanwhile, the handle part 100 moves while rotating so that foreign materials are not pinched in the handle part 100.

Although the present invention has been described above with reference to the accompanying drawings, the present invention is not limited by the embodiments and drawings illustrated in the present specification, and it is clear that the present invention can be variously modified by those skilled in the art within a range of the technical spirit of the present invention. In addition, even if operational effects according to the structure of the present invention have not been clearly described in description of the embodiments of the present invention, predictable effects according to the corresponding structure should also be recognized.

The invention claimed is:

1. A door handle comprising:
   a housing fixable to a door and having an inner space;
   a driving motor positioned inside the housing, the driving motor being configured to supply rotational power;
   a rotating guide connected to the driving motor to receive the rotational power to rotate inside the housing; and
   a handle member positioned on the rotating guide, the handle member having guide protrusions, wherein the handle member protrudes outward from the housing upon forward rotation of the rotating guide,
wherein the handle member is accommodated inside the housing upon reverse rotation of the rotating guide,
wherein the housing includes:
  a mounting member fixable to the door and configured to restrict movement of the driving motor;
  a case fixed to the mounting member and surrounding an outer circumference of the rotating guide; and
  a fixing guide fixed inside the case, the fixing guide including holes, and
wherein the holes of the fixing guide are configured to guide movement of the guide protrusions.

2. The door handle of claim 1, wherein the handle member includes:
  a handle body positioned inside the rotating guide; and
  the guide protrusions, the guide protrusions extending radially outward from the handle body.

3. The door handle of claim 2, wherein the handle body includes:
  a first handle body having a side surface, the guide protrusions being fixed to the side surface of the first handle body; and
  a second handle body connected to the first handle body, the second handle body being configured to protrude outward from the housing with rotation of the first handle body.

4. The door handle of claim 3, wherein the second handle body includes:
  a second handle frame including:
    a first side fixed to the first handle body; and
    a second side spaced apart from the first handle body; and
  a door pull disposed in a side surface of the second handle frame facing the first handle body, the door pull having a concave groove shape.

5. The door handle of claim 4, wherein the second handle body further includes:
  a second handle cover covering an open portion of the second handle frame; and
  a lighting device positioned between the second handle cover and the second handle frame, the lighting device being configured to emit light toward an outside of the second handle cover.

6. The door handle of claim 5, wherein the second handle body further includes a light guide having a ring shape and positioned along an outer circumference of the lighting device, the light guide being configured to diffuse light emitted from the lighting device.

7. The door handle of claim 4, further comprising a sterilizer positioned in the handle member, the sterilizer being configured to emit sterilizing light to disinfect the handle member.

8. The door handle of claim 7, wherein the sterilizer is positioned in the first handle body, and
  wherein the sterilizer emits the sterilizing light toward the door pull.

9. The door handle of claim 1, wherein the fixing guide includes:
  a guide body having a cylindrical shape and including a first side obliquely cut and a second side fixed to the mounting member, and
  wherein the holes of the fixing guide include:
    a first guide hole provided in the guide body and having a spiral shape, the first guide hole being configured to guide movement of a first one of the guide protrusions; and
    a second guide hole provided in the guide body and having a spiral shape, the second guide hole being configured to guide movement of a second one of the guide protrusions.

10. The door handle of claim 9, wherein the rotating guide includes:
  a rotating guide body rotatably installed inside the housing and connected to the driving motor to rotate; and
  a guide slot provided in the rotating guide body and facing the first guide hole and the second guide hole, the guide slot being configured to guide the movement of the guide protrusions.

11. The door handle of claim 10, wherein the rotating guide body includes:
  a rotation base having a plate shape;
  a connection rib positioned in a rotational center of the rotation base, the connection rib being connected to the driving motor; and
  a guide sidewall extending from the rotation base, the guide sidewall being positioned inside the housing, and
  wherein the guide slot is positioned at an inner side of the guide sidewall.

12. The door handle of claim 10, wherein the guide slot includes:
  a first guide slot configured to guide the movement of the first one of the guide protrusions provided at a first side of the handle member, the first guide slot facing the first guide hole; and
  a second guide slot configured to guide the movement of the second one of the guide protrusions provided at a second side of the handle member, the second guide slot facing the second guide hole.

13. The door handle of claim 12, wherein the first guide slot includes:
  a first straight groove extending in a longitudinal direction of the housing,
  a first upper groove having a shape bent from a first side of the first straight groove; and
  a first lower groove having a shape bent from a second side of the first straight groove, and
  wherein the first upper groove and the first lower groove extend in opposite directions from the first straight groove.

14. The door handle of claim 13, wherein the second guide slot includes:
  a second straight groove extending in the longitudinal direction of the housing;
  a second upper groove having a shape bent from a first side of the second straight groove; and
  a second lower groove having a shape bent from a second side of the second straight groove, and
  wherein the second upper groove and the second lower groove extend in opposite directions from the second straight groove.

15. The door handle of claim 1, wherein the handle member includes the guide protrusions protruding from the handle member, the guide protrusions being spaced apart from one another,
  wherein the housing includes a first guide hole and a second guide hole, the first guide hole and the second guide hole being configured to guide forward and backward movement of the guide protrusions, and
  wherein the rotating guide includes:
    a first guide slot facing the first guide hole; and
    a second guide slot facing the second guide hole.

16. The door handle of claim 15, wherein with forward rotation of the driving motor:

the rotating guide is configured to be rotated, the guide protrusions are configured to be rotated in a forward direction along the first guide hole and the second guide hole, and the handle member is configured to protrude outward from the housing.

17. The door handle of claim 15, wherein with reverse rotation of the driving motor:

the rotating guide is configured to be rotated, the guide protrusions are configured to be rotated in a reverse direction along the first guide hole and the second guide hole, and the handle member is configured to be moved into the housing.

18. The door handle of claim 15, wherein the first guide slot includes:

a first straight groove extending in a longitudinal direction of the housing, the first straight groove being configured to guide a movement of a first one of the guide protrusions;

a first upper groove having a shape bent from a first side of the first straight groove; and a first lower groove having a shape bent from a second side of the first straight groove, and wherein the first upper groove and the first lower groove extend in opposite directions from the first straight groove.

19. The door handle of claim 18, wherein the second guide slot includes:

a second straight groove extending in the longitudinal direction of the housing, the second straight groove being configured to guide a movement of a second one of the guide protrusions;

a second upper groove having a shape bent from a first side of the second straight groove; and a second lower groove having a shape bent from a second side of the second straight groove, and wherein the second upper groove and the second lower groove extend in opposite directions from the second straight groove.

20. A door handle comprising:

a housing fixable to a door;

a driving motor located inside the housing, the driving motor being configured to supply rotational power;

a rotating guide connected to the driving motor to receive the rotational power to rotate; and a handle member located on the rotation guide, the handle member having guide protrusions the handle member being configured to move in forward and backward directions of the housing by forward and reverse rotations of the rotation guide, and wherein the housing includes:

a mounting member fixable to the door and configured to restrict movement of the driving motor;

a case fixed to the mounting member and surrounding an outer circumference of the rotating guide; and a fixing guide fixed inside the case, the fixing guide including holes, and wherein the holes of the fixing guide are configured to guide movement of the guide protrusions.

21. The door handle of claim 20, wherein the handle member includes:

a handle body positioned inside the rotating guide;

the guide protrusions, the guide protrusions extending radially outward from the handle body and are configured to rotate within guide holes of the rotating guide and within the holes of the housing; and a sterilizer configured to emit sterilizing light to disinfect the handle member.

* * * * *